(12) United States Patent
Kondo et al.

(10) Patent No.: US 7,695,440 B2
(45) Date of Patent: Apr. 13, 2010

(54) BLOOD PRESSURE MEASURING APPARATUS

(75) Inventors: Akira Kondo, Fujinomiya (JP); Takashi Watanabe, Fujinomiya (JP); Masaru Nakanishi, Fujinomiya (JP); Shuichi Oonishi, Fujinomiya (JP); Hitoshi Ozawa, Fujinomiya (JP); Naoe Tatara, Atsugi (JP); Shoichi Hayashida, Atsugi (JP)

(73) Assignees: Terumo Kabushiki Kaisha, Shibuya-Ku, Tokyo (JP); Nippon Telegraph and Telephone Corporation, Chiyoda-Ku, Tokyo (JP)

( * ) Notice: Subject to any disclaimer, the term of this patent is extended or adjusted under 35 U.S.C. 154(b) by 166 days.

(21) Appl. No.: 11/902,351

(22) Filed: Sep. 20, 2007

(65) Prior Publication Data
US 2008/0091113 A1    Apr. 17, 2008

Related U.S. Application Data

(63) Continuation of application No. PCT/JP2006/305952, filed on Mar. 24, 2006.

(30) Foreign Application Priority Data

Apr. 8, 2005    (JP)    ............................. 2005-112570
Apr. 8, 2005    (JP)    ............................. 2005-112573

(51) Int. Cl.
*A61B 5/02*    (2006.01)

(52) U.S. Cl. ....................... 600/485; 600/500
(58) Field of Classification Search ................. 600/485, 600/490
See application file for complete search history.

(56) References Cited

U.S. PATENT DOCUMENTS 3,412,729 A   *   11/1968   Smith, Jr. ..................... 600/324

(Continued)

FOREIGN PATENT DOCUMENTS

JP      6-55603 U      8/1994

(Continued)

OTHER PUBLICATIONS

PCT/ISA/210 and PCT/ISA/237 for PCT/JP12006/305952 dated Apr. 25, 2006.

(Continued)

*Primary Examiner*—Charles A Marmor, II
*Assistant Examiner*—Christian Y Jang
(74) *Attorney, Agent, or Firm*—Buchanan Ingersoll & Rooney PC

(57) ABSTRACT

A blood pressure measurement apparatus which can install cuffs at a tragus that has differences includes a holding member 3 having a shape part 52 to be installed in a space between an auricular concha and an antihelix, a first protrusion 54 extended from the shape part such that the first protrusion is directed towards the ear hole, a second protrusion 55 extended from the shape part such that the second protrusion is nearly right-angled with respect to the first protrusion and the second protrusion steps over the tragus, an integral member 50 having an ear hook part 51 that is extended from the shape part, the ear hook is integrally made with the integral member or made as an independent member, inner cuff 6 is supported at the end portion of the first protrusion, support member 15 is attached at the end portion of the second protrusion, cuffs 6,7 are attached to the support member through a clamping width adjustment part 11 that makes a clamping width adjustment against the tragus possible.

15 Claims, 26 Drawing Sheets

U.S. PATENT DOCUMENTS

| | | |
|---|---|---|
| 6,873,865 B2 | 3/2005 | Steuer et al. |
| 2002/0041697 A1* | 4/2002 | MacDonald et al. ........ 381/381 |
| 2005/0049468 A1* | 3/2005 | Carlson et al. .............. 600/323 |

FOREIGN PATENT DOCUMENTS

| | | |
|---|---|---|
| JP | 2005-6906 A | 1/2005 |
| WO | WO 2005/034742 A1 | 4/2005 |

OTHER PUBLICATIONS

Notice of Allowance issued in corresponding TW Patent Application No. 095110703, Aug. 21, 2008, Taiwan Intellectual Property Office, TW; and English-language translation thereof.

English language version of Written Opinion of the International Searching Authority and English language version of International Preliminary Report on Patentability, both issued in corresponding International Application No. PCT/JP2006/305952.

Osamu Tochikubo, "Measurement Method and Clinical Evaluation of Blood Pressure", Medical Tribune Ltd., 1998, pp. 59-61 (Partial English translation).

* cited by examiner

BLOOD PRESSURE MEASURING APPARATUS

TECHNICAL FIELD

The present invention relates to a blood pressure measuring apparatus and, more particularly, to a technique that uses the external ear and its periphery as portions to be measured.

BACKGROUND ART

The blood pressure changes momentarily in accordance with changes in external and internal environments. Therefore, it is ideal to be able to continuously record heartbeats one after another. Although such continuous recording is impossible, it is important to provide health care by measuring the change in blood pressure with time by periodically (intermittently) measuring the blood pressure over the course of a day.

When periodically measuring the blood pressure by the conventional blood pressure measuring apparatus, the blood pressure is measured by winding a cuff around the brachium of a person to be measured. In this case, it is necessary to attach, to the body, a large cuff that covers the brachium and the main body of the blood pressure measuring apparatus connected to the cuff. When periodically measuring the blood pressure by the blood pressure measuring apparatus, therefore, a person to be measured must always have the cuff attached to the brachium and the main body of the blood pressure measuring apparatus connected to the cuff being attached to the body. This largely interferes with everyday life. There is also a burden on the person to be measured; he or she may feel pain because the brachium is pressed whenever the blood pressure is measured.

In order to solve such problems, instead of measuring a blood pressure at a brachium, there is a blood measuring method for measuring the blood pressure by winding small cuff on the fingers. According to this measuring method, because the size of the finger is small compared with the brachium, the cuff and the main body can be made small (non patent reference 1). There is also a method that measures the pulse wave by attaching a cuff to the earlobe and pressing it (patent reference 1).

This method can make the cuff and main body smaller than a sphygmomanometer that measures the blood pressure by attaching a cuff to the brachium, and can also reduce the burden on a person to be measured.

Non-Patent Literature 1:

Osamu TOCHIKUBO, "Measurement method and clinical evaluation of blood pressure", issued in Medical Tribune Ltd. in 1988, pages 59-61

Patent reference 1: Japanese Patent Laid-Open No. 2005-6906

DISCLOSURE OF INVENTION

Problems that the Invention is to Solve

Even when measuring the pulse wave or blood pressure in the earlobe, however, it is difficult to stably and accurately measure the blood pressure because the blood vessels in the earlobe are very thin. In particular, the blood vessels in the earlobe shrink when the external temperature lowers, and this makes stable measurement more difficult.

If, therefore, the blood pressure or the like is measured by attaching the cuff to the tragus in which the blood vessels are thicker than those of the earlobe, it is presumably possible to stably measure the blood pressure relatively close to that in the brachium.

Unfortunately, although the cuff can be easily attached to the earlobe because it is soft, relatively large, and largely exposed, the tragus is relatively hard and has a large difference in shape between individuals, so the structure of the earlobe cuff disclosed in patent reference 1 cannot be directly diverted to the tragus. That is, even when the structure of the attaching portion disclosed in patent reference 1 is used, it is difficult to stably obtain the results of blood pressure measurement in the tragus. Also, if the cuff is attached to the tragus by force, the degree of invasion to the person to be measured may increase.

On the other hand, the tragus is known to have great individual differences in a relative position with respect to the external ear, shape and the size, etc. Moreover, in order to accurately measure blood pressure, it becomes necessary to maintain the state that inner and outer cuff can surely come in contact with the tragus.

Therefore, this invention is made in view of these circumstances, and has its object to provide a blood pressure measurement apparatus which can accurately measure blood pressure, by ensuring that the inner and outer cuffs surely come into contact with the tragus when the inner and outer cuff is installed in the tragus while maintaining positions corresponding well to an individual difference in the tragus shape.

Another object of the present invention is to provide a blood pressure measurement apparatus that is more miniaturized, can reduce the unpleasantness to those who install the apparatus, and is easy to carry.

Means of Solving the Problems

To solve the above problem, a blood pressure measuring apparatus according to the present invention is characterized by comprising: an inner cuff to be inserted into an ear hole, and an outer cuff to be positioned outside a tragus; holding means for holding said inner cuff and said outer cuff; pulse wave detecting means incorporated into at least one of said inner cuff and said outer cuff to detect a pulse wave signal from blood flowing through a blood vessel; pressurizing/depressurizing means for pressurizing and depressurizing said inner cuff and said outer cuff by using a fluid, after said inner cuff and said outer cuff clamp the tragus; a tube connected from said inner cuff and said outer cuff to said pessurizing/depressurizing means to supply the fluid; pressure detecting means connected to said tube to detect pressures of said inner cuff and said outer cuff; and blood pressure measurement control means for measuring a blood pressure value from the pulse wave signal, wherein said holding means comprises;

a shape part to be installed in a space between an auricular concha and an antihelix, a first protrusion extended from said shape part such that said first protrusion is directed towards the ear hole, a second protrusion extended from said shape part such that said second protrusion is nearly right-angled with respect to said first protrusion and said second protrusion steps over the tragus, an integral member having an ear hook that is extended from said shape part, said ear hook is integrally made with said integral member or made as an independent member, and wherein said integral member supports said inner cuff at an end portion of said first protrusion, said integral member fixes a support member at an end portion of said second protrusion, said outer cuff is attached to said support member through a clamping width adjustment part that makes a clamping width adjustment against the tragus possible.

The apparatus is characterized in that said outer cuff is comprised of a first outer cuff and a second outer cuff, said first outer cuff and said second outer cuff are fixed to a cuff member having a channel communicating said tube, such that said first outer cuff and said second outer cuff are located in the up and down directions with respect to the tragus, said cuff member is attached at an end portion of said support member through said clamping width adjustment part.

The apparatus is characterized in that said support member is attached to said second protrusion such that said support member is adjustable in the up and down directions with respect to the tragus.

The apparatus according is characterized in that said inner cuff is fixed to said first protrusion such that said inner cuff is possible to rotate and invasion degree into the ear hole is adjustable, and said inner cuff can be pressurized and depressurized through an inner tube provided in said first protrusion.

The apparatus is characterized in that said clamping width adjustment part comprises a ball bearing part provided on the end portion, wherein said ball bearing part supports said outer cuff such that said outer cuff can move with neck movement.

The apparatus is characterized in that a first adjustment screw for adjusting said support member in the up and down directions with respect to said second protrusion is provided, wherein said first adjustment screw maintains a state after the adjustment.

The apparatus is characterized in that said clamping width adjustment part is a one-direction movement member comprising a male screw screwed into a female hole formed at the other end of said support member, or one direction movement member comprising a plurality of flexible jaws on the outer surface which maintains the inserted state after being inserted into a hole.

The apparatus is characterized in that said pulse wave detecting means, said pressurizing/depressurizing means and said blood pressure measurement control means are incorporated into a main body of the apparatus, wherein main body and said holding means supporting said inner cuff and said outer cuff are connected by said tube and a wire connected between said pulse wave detecting means and said blood pressure measurement control means.

The blood pressure measuring apparatus is characterized by comprising: an inner cuff to be inserted into an ear hole, and an outer cuff to be positioned outside a tragus; holding means for holding said inner cuff and said outer cuff; pulse wave detecting means incorporated into at least one of said inner cuff and said outer cuff to detect a pulse wave signal from blood flowing through a blood vessel; an ear hook part extended from said holding means; a blood pressure measurement main body directly attached to said ear hook part, and positioned behind the rear portion of the auricle when installed; wherein said blood pressure measurement main body comprises; pressurizing/depressurizing means for pressurizing and depressurizing said inner cuff and said outer cuff by using a fluid; blood pressure measurement control means for measuring a blood pressure value from the pulse wave signal; wherein said inner cuff, said outer cuff and said pressurizing/depressurizing means are connected by a fluid sending tube for sending said fluid.

The apparatus is characterized in that said fluid sending tube is incorporated in said ear hook part.

The apparatus is characterized in that said holding means comprises; a shape part to be installed in a space between an auricular concha and an antihelix, a first protrusion extended from said shape part such that said first protrusion is directed towards the ear hole, a second protrusion extended from said shape part such that said second protrusion is nearly right-angled with respect to said first protrusion and said second protrusion steps over the tragus, an integral member having said ear hook that is integrally extended from said shape part.

The apparatus is characterized in that an ear contact point against the antihelix of said shape part is made of softer materials than other parts.

The apparatus is characterized in that said clamping width adjustment part has a neck movement mechanism at the end potion wherein said outer cuff can move with neck movement.

The apparatus is characterized in that said support member is attached to said second protrusion such that said support member is adjustable in the up and down directions with respect to the tragus.

The apparatus is characterized in that said main body has a larger curve radius at the user's head contact side than the user's head non-contact side.

Other features of the present invention will be apparent below from the best mode for carrying out the invention and the accompanying drawings.

EFFECTS OF THE INVENTION

According to the present invention, by setting the cuff installation part into the space between the auricular concha and the antihelix, and by further using an ear hook of the apparatus, installation stability is secured. Thus an accurate blood pressure measurement becomes possible because inner and outer cuffs can come into contact with the tragus evenly.

According to the present invention, the ear hook to be mounted on the helix is directly attached to the main body of the blood pressure apparatus. Therefore, the miniaturization of the apparatus itself becomes possible because the necessity for lay pipes for sending and exhausting the fluid such as air to and from the separated main body is not needed, and never disturbed by twisted pipes.

According to the present invention, by setting the cuff installation part into the space between the auricular concha and the antihelix, and by further using the ear hook of the apparatus, installation stability is secured. Thus an accurate blood pressure measurement becomes possible because inner and outer cuffs can come into contact with the tragus evenly.

Other features and advantages of the present invention will be apparent from the following explanation taken in conjunction with the accompanying drawings. Note that the same reference numerals denote similar arrangements or the same arrangements in the accompanying drawings.

EXPLANATION OF NUMERALS

1 Ear type blood pressure measuring apparatus
2 Main body
3 Holding member
4 Tube
5 Cable (signal and power supply line)
6 Inner cuff assembly body
7 First outer cuff assembly body
8 Second outer cuff assembly body
9 Cover member
10 Support member
11 Clamping width adjustment screw
12 Branch pipe
13 First support member
14 Second support member 15 Third support member
17 Spacer
18 The first adjustment screw
19 The second adjustment screw
20 Luminescence element (LED)
21 Photodetectors (photo transistor)
22, 23 Cuff bladder
24 O ring
25 Contact surface
26 Flange part
27 Bellows part
28 Opening
38 Engagement member
42 Seal agent
44 Internal wall surface
45 Shading layer
46 Opening
50 Brushing bush
51 Ear hook part
52 Shape part
53 Internal piping
54 First protrusion
55 Second protrusion

BRIEF DESCRIPTION OF DRAWINGS

The accompanying drawings are included in the specification, constitute part of the specification, illustrate embodiments of the present invention, and are used to explain the principle of the present invention together with the description.

Figure 1:
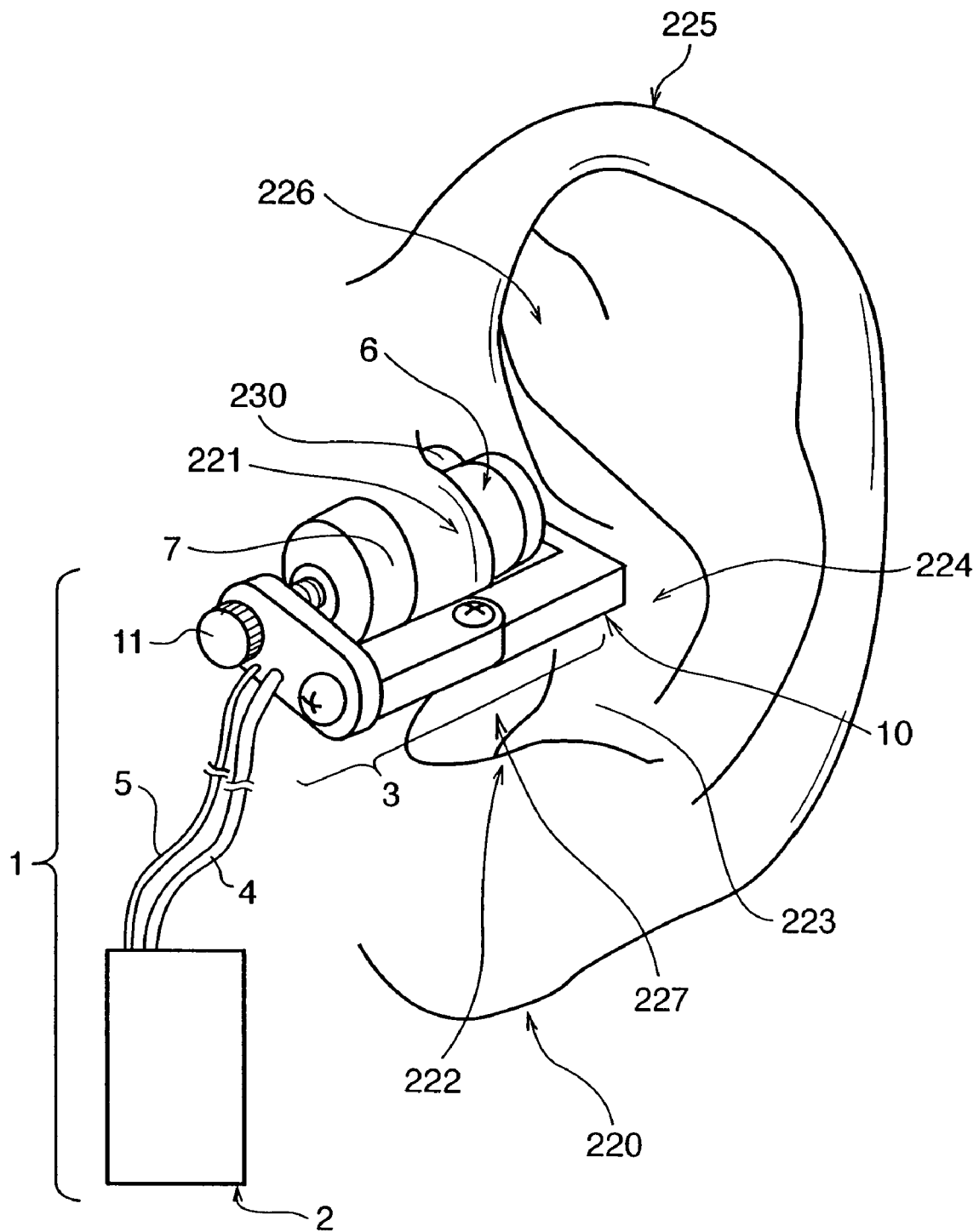
FIG. 1 is an outer appearance perspective view showing the state in which the blood pressure measuring apparatus 1 according to the present invention is used for the auricle.
Figure 6:
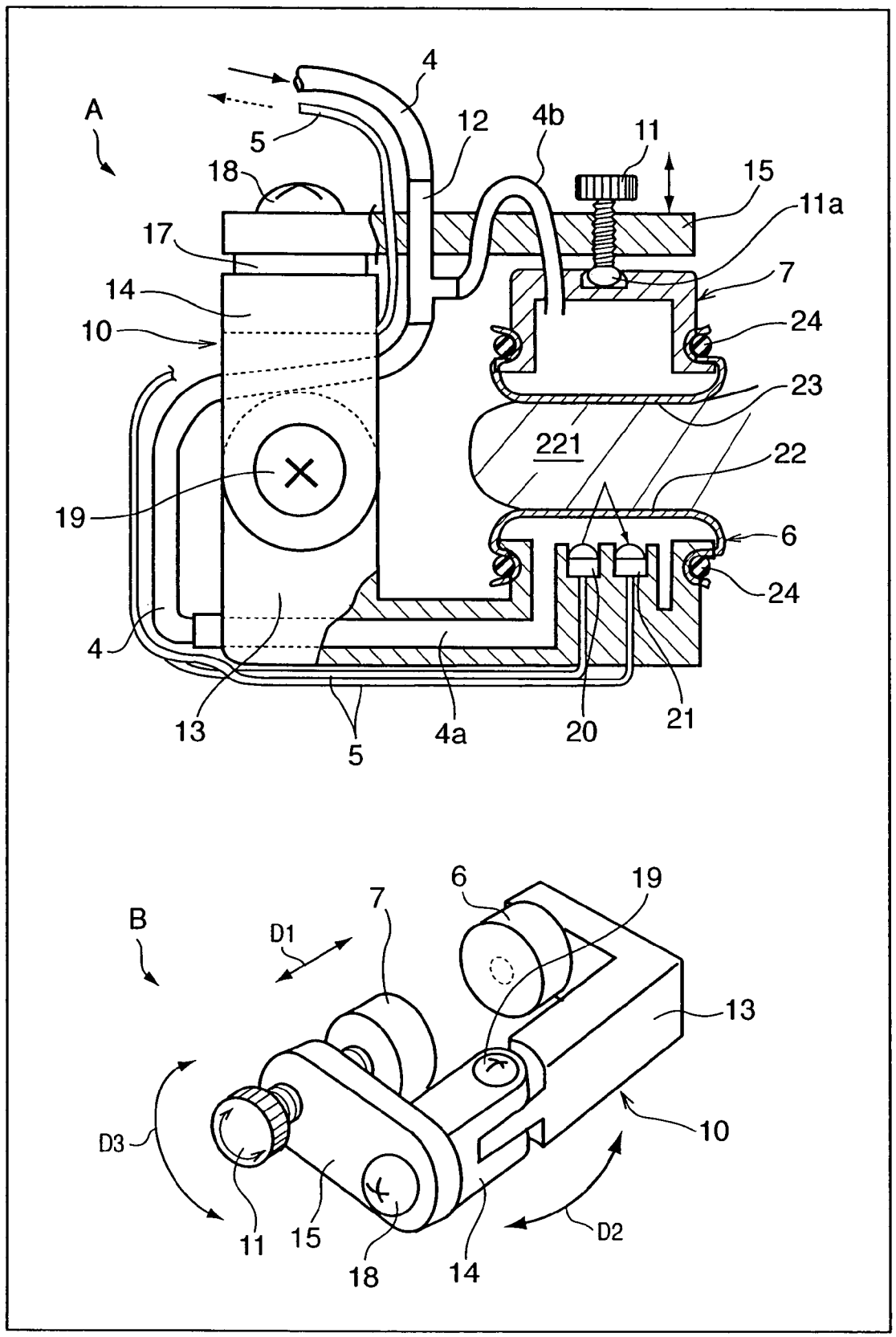
Figure 7:
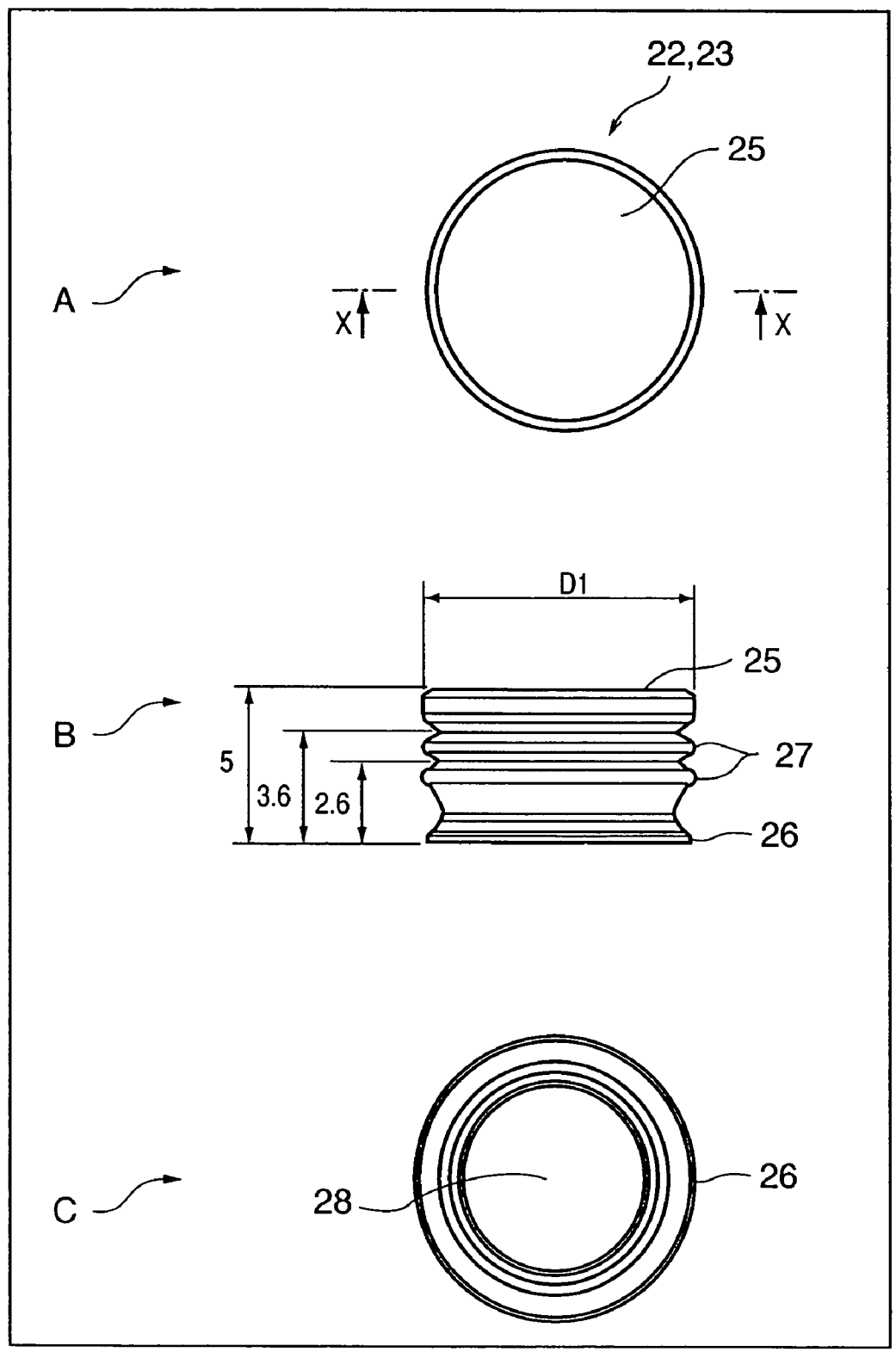
Figure 8:
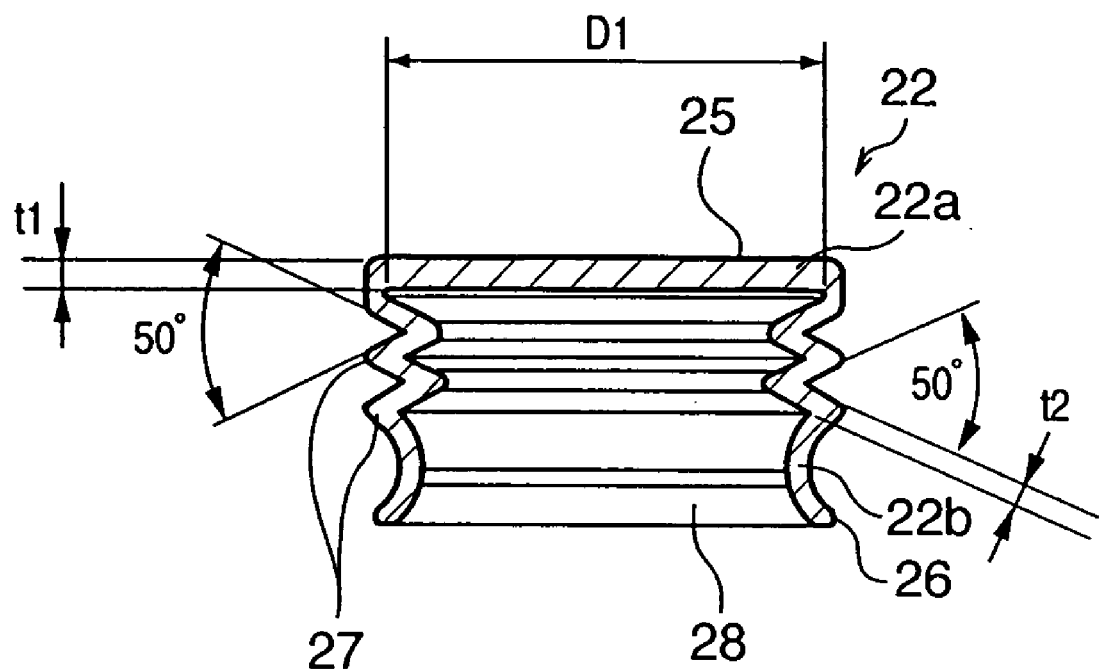
Figure 9:
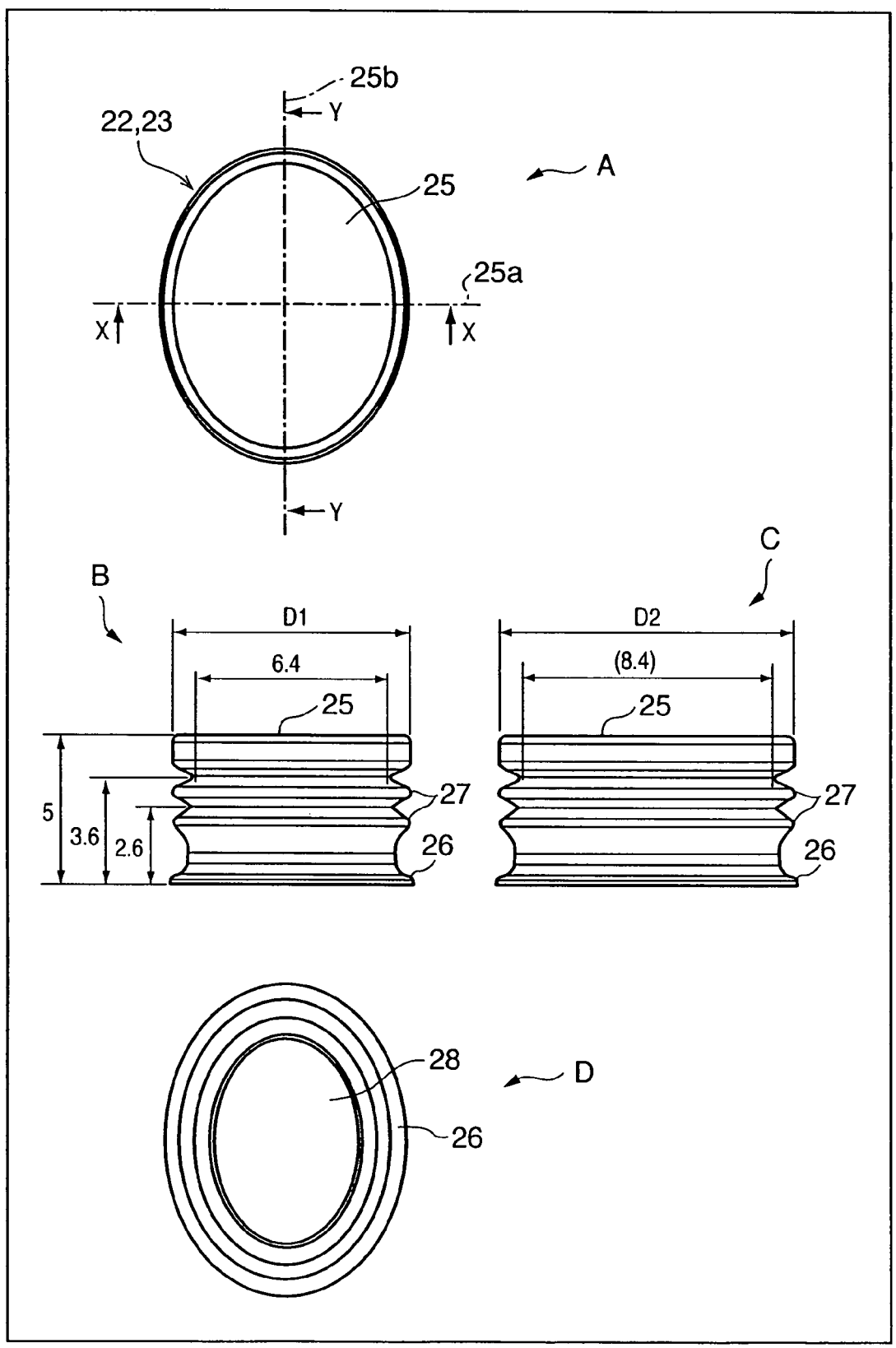
Figure 10:
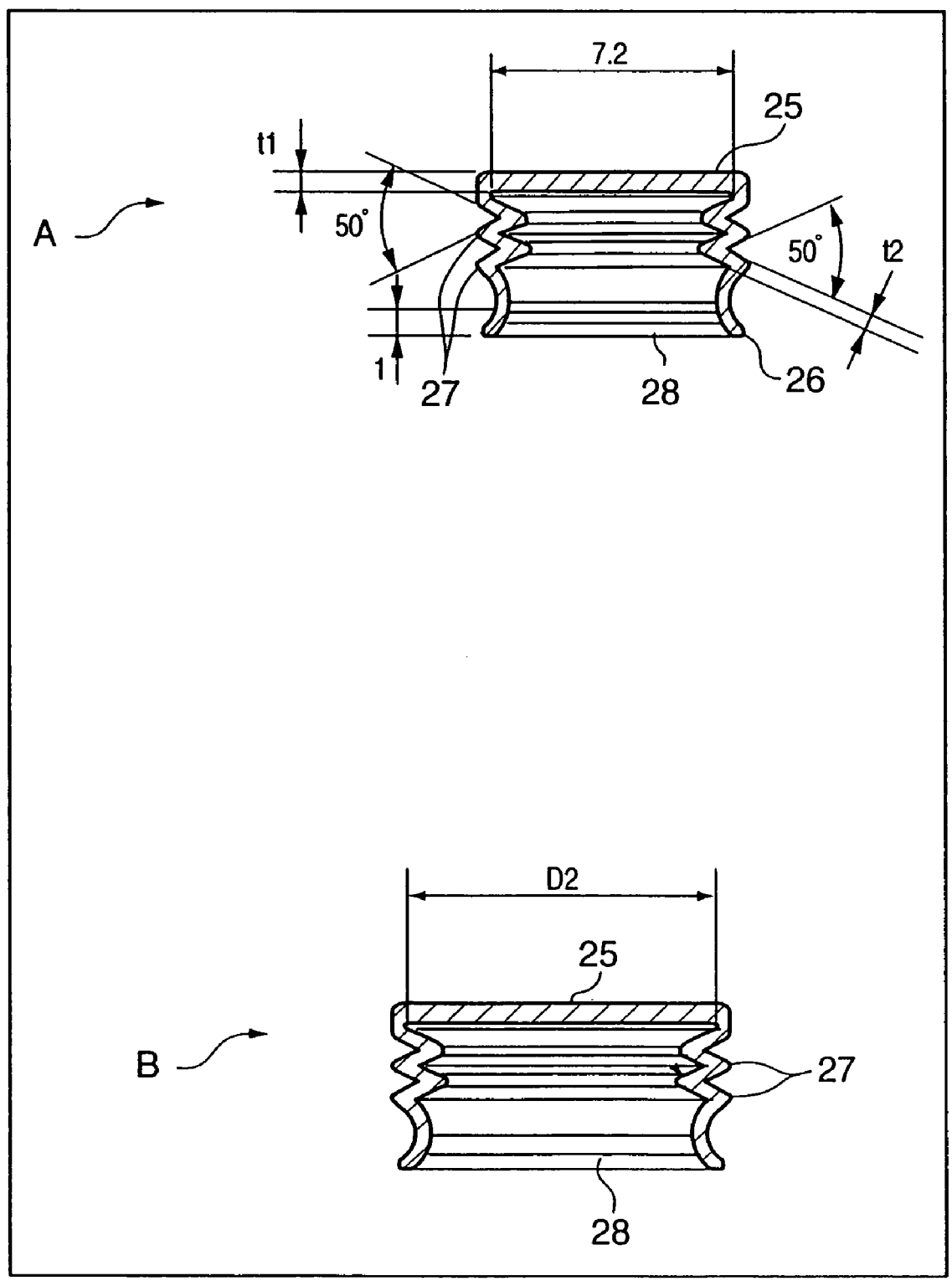
Figure 11:
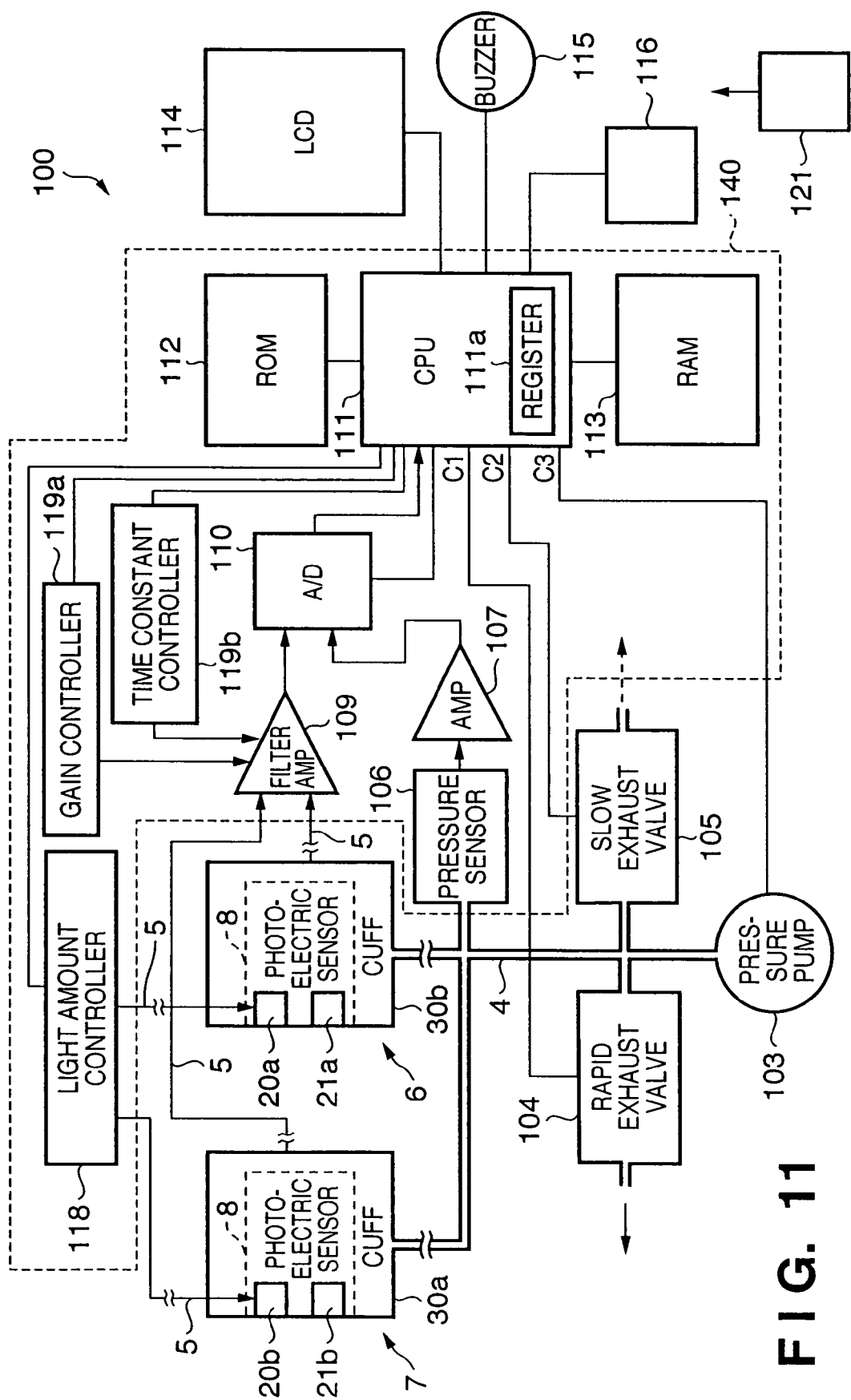
Figure 12:
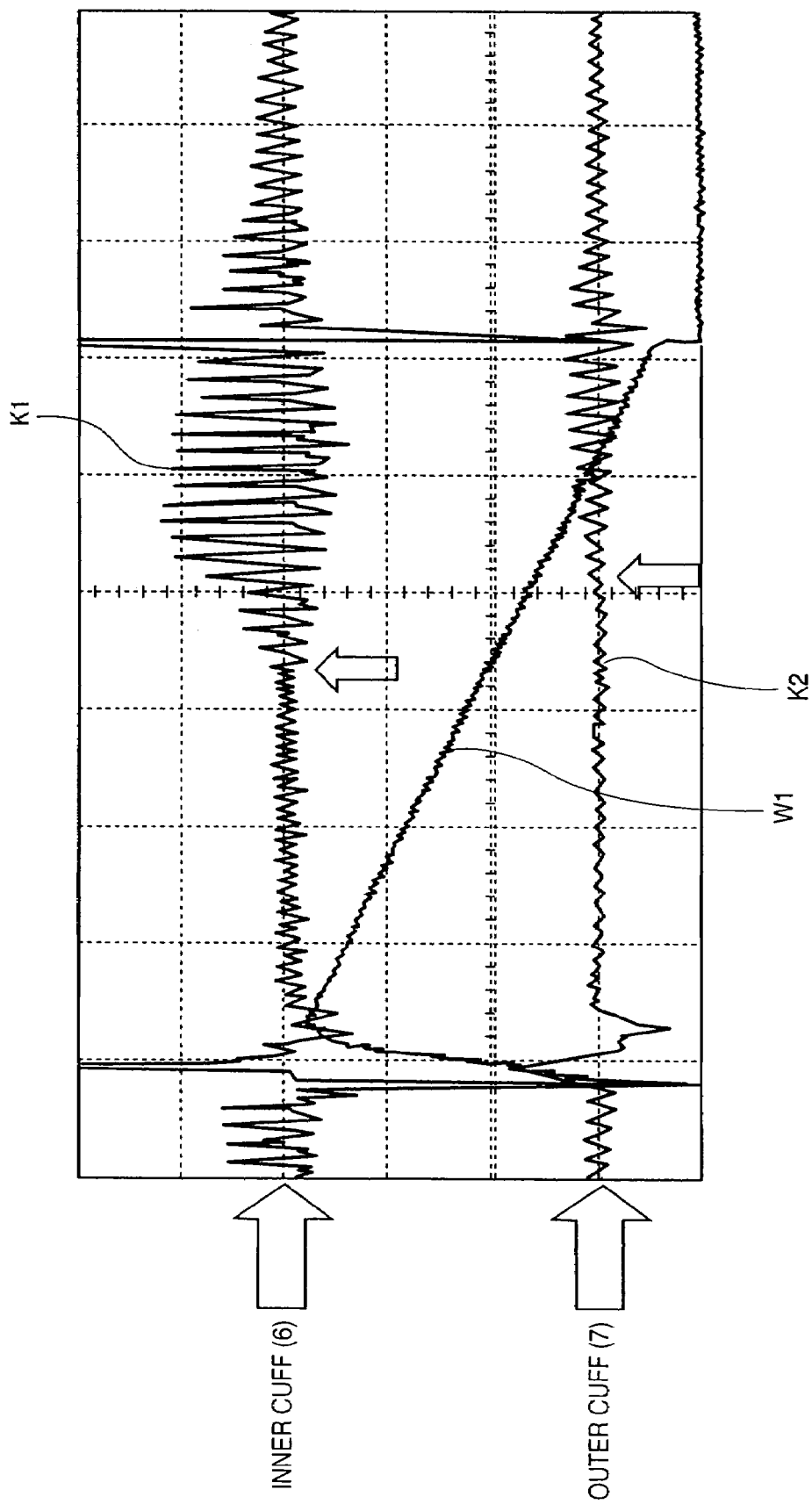
Figure 13:
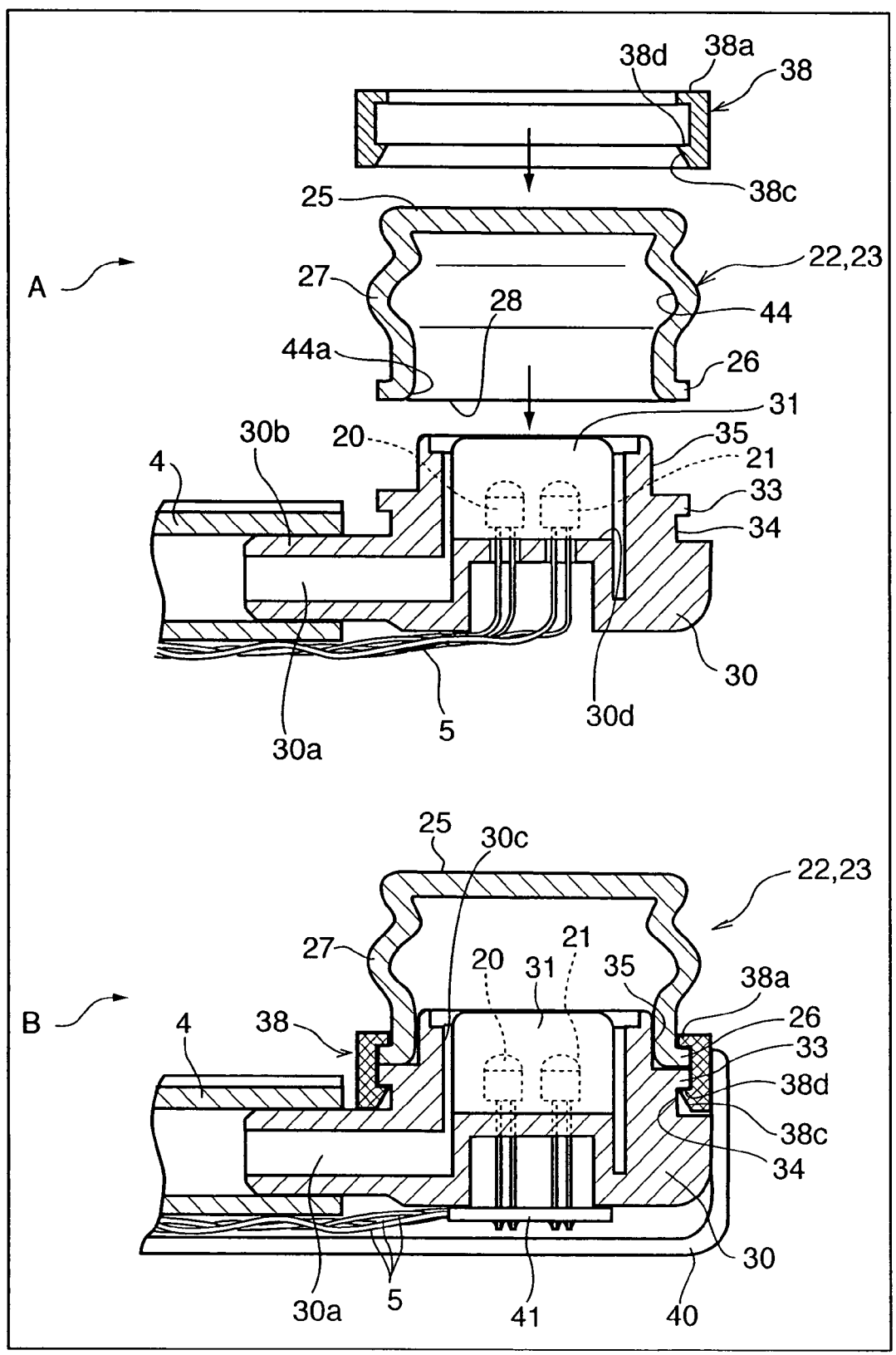
Figure 14:
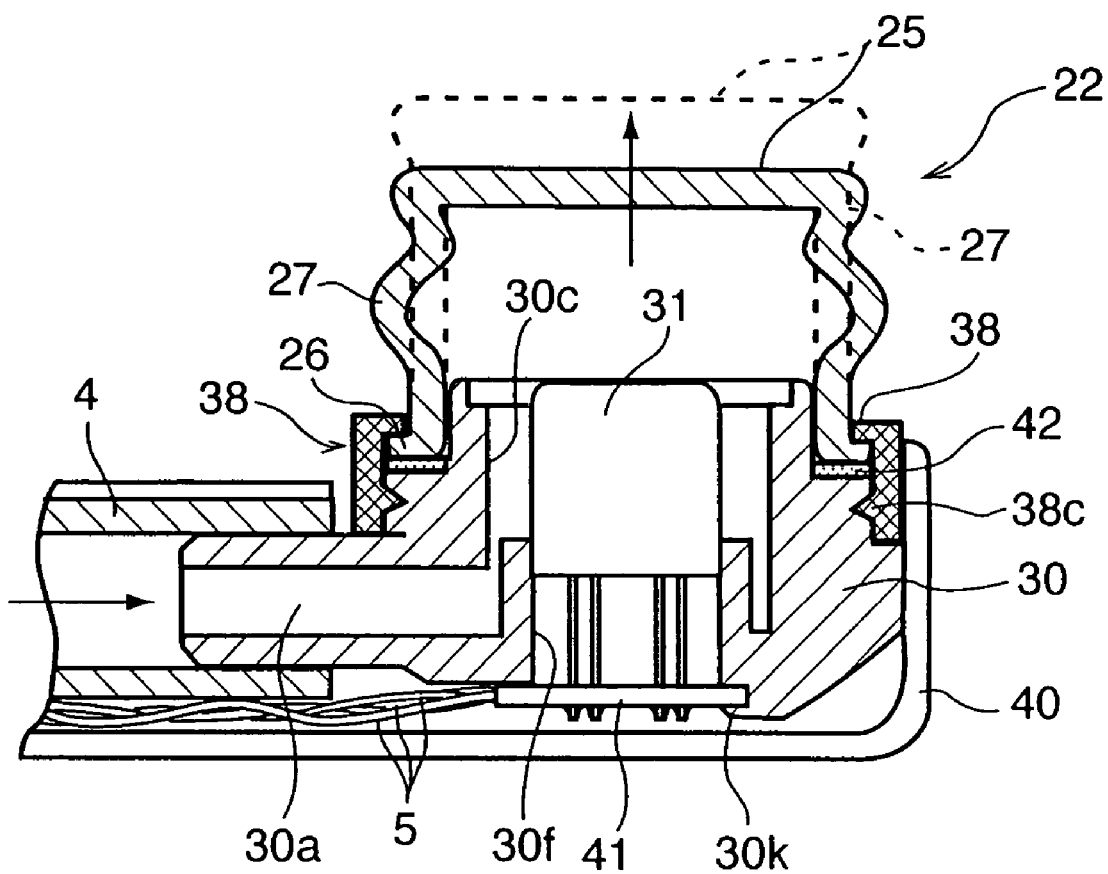
Figure 15:
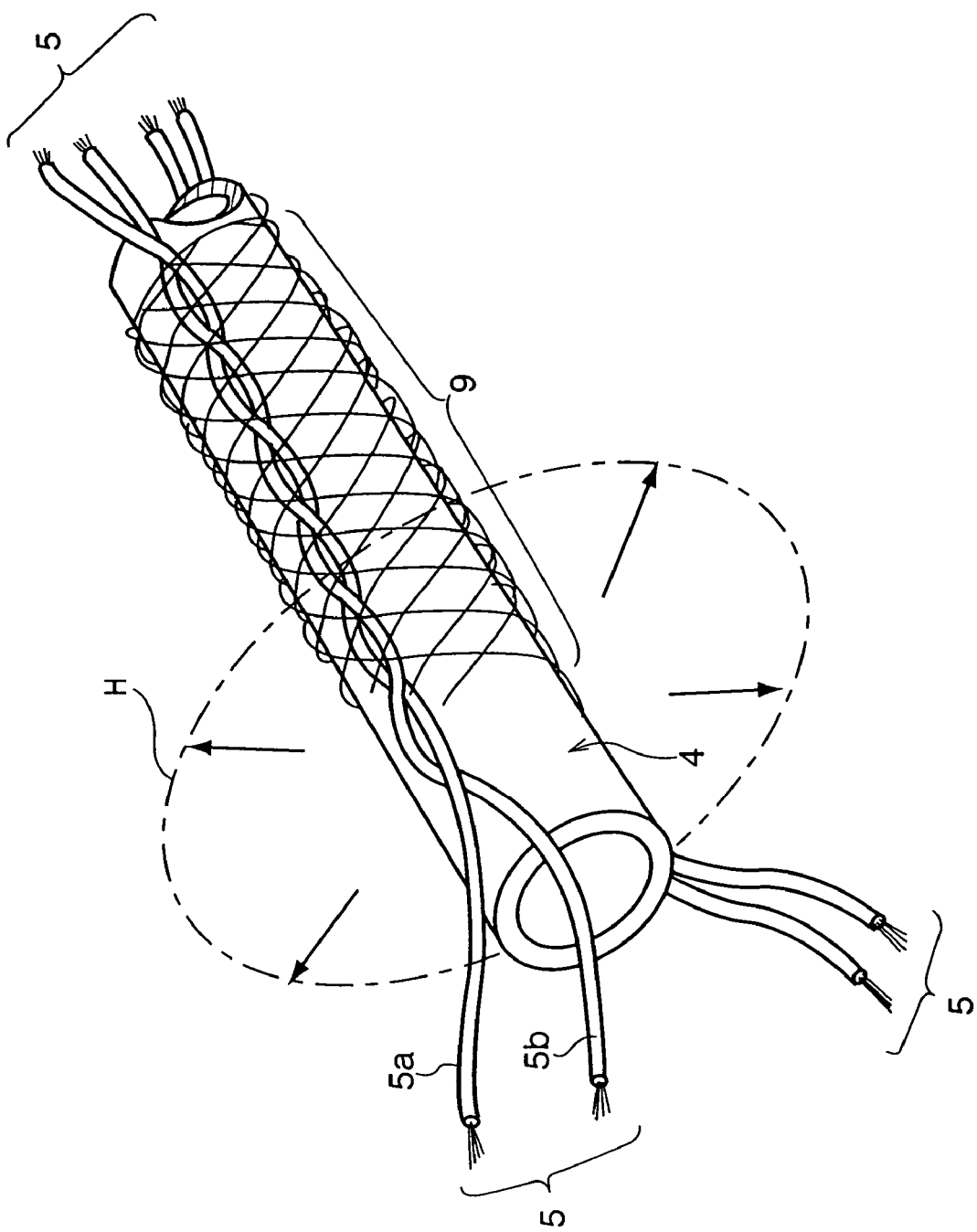
Figure 16:
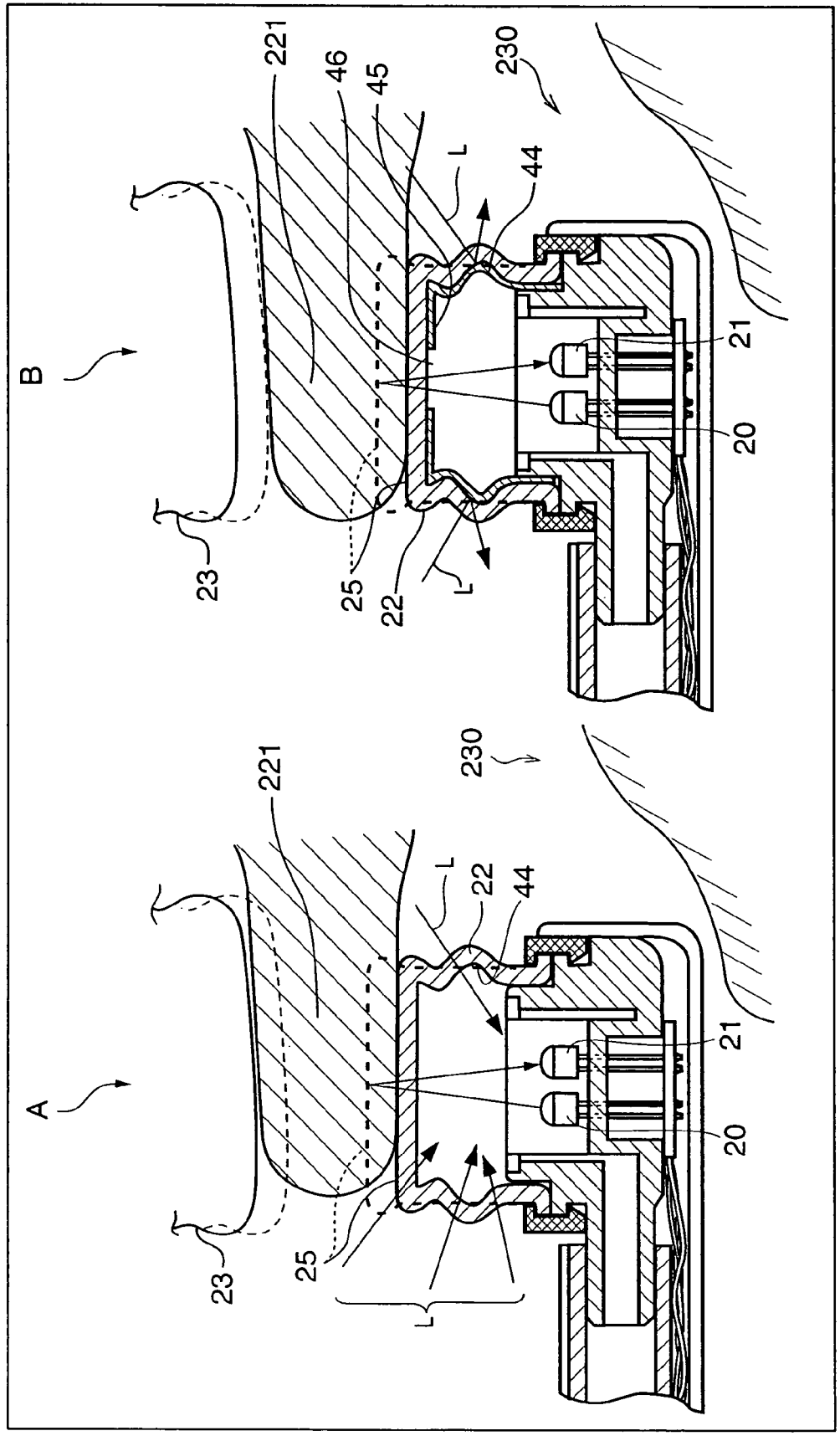
Figure 17:
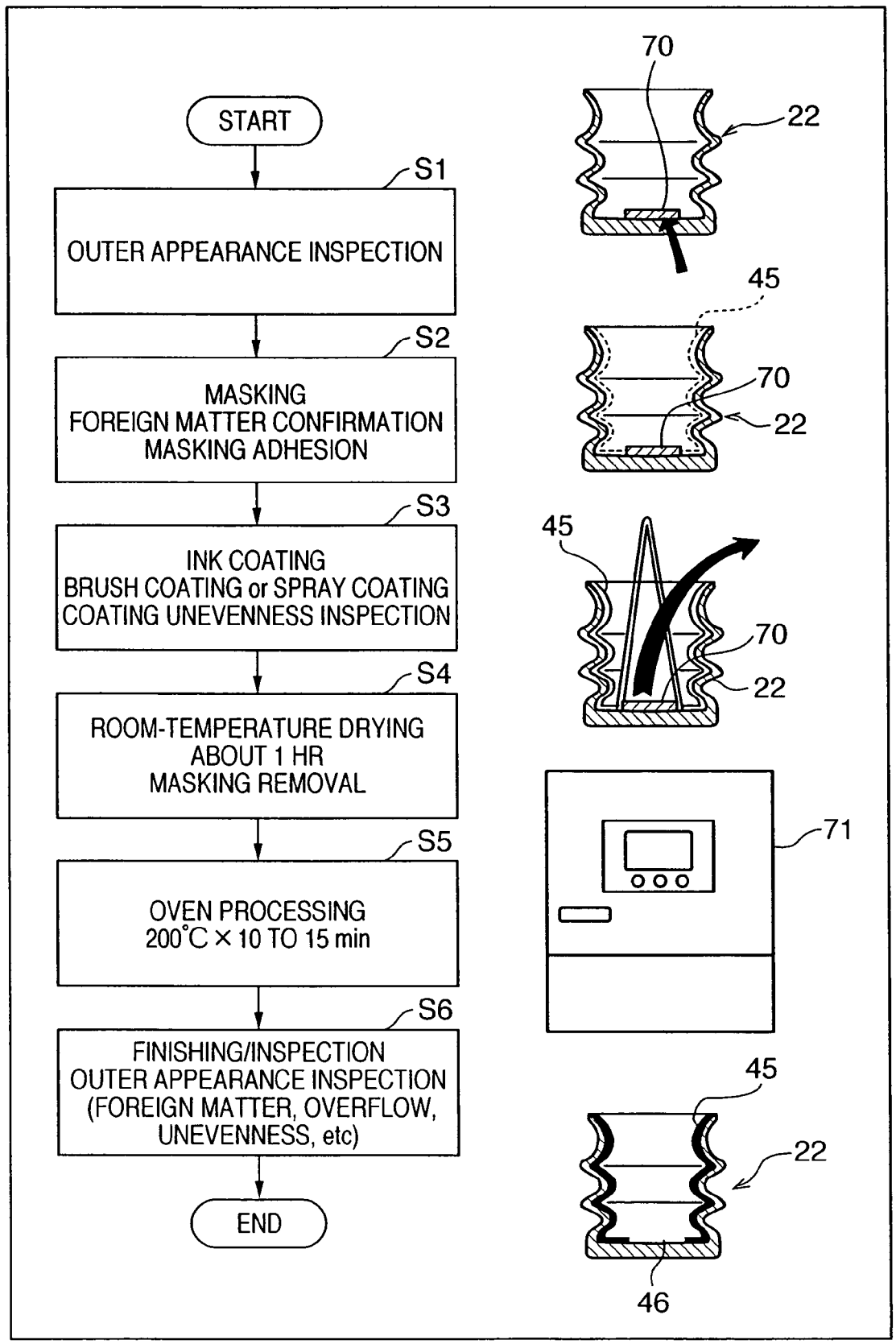
Figure 18:
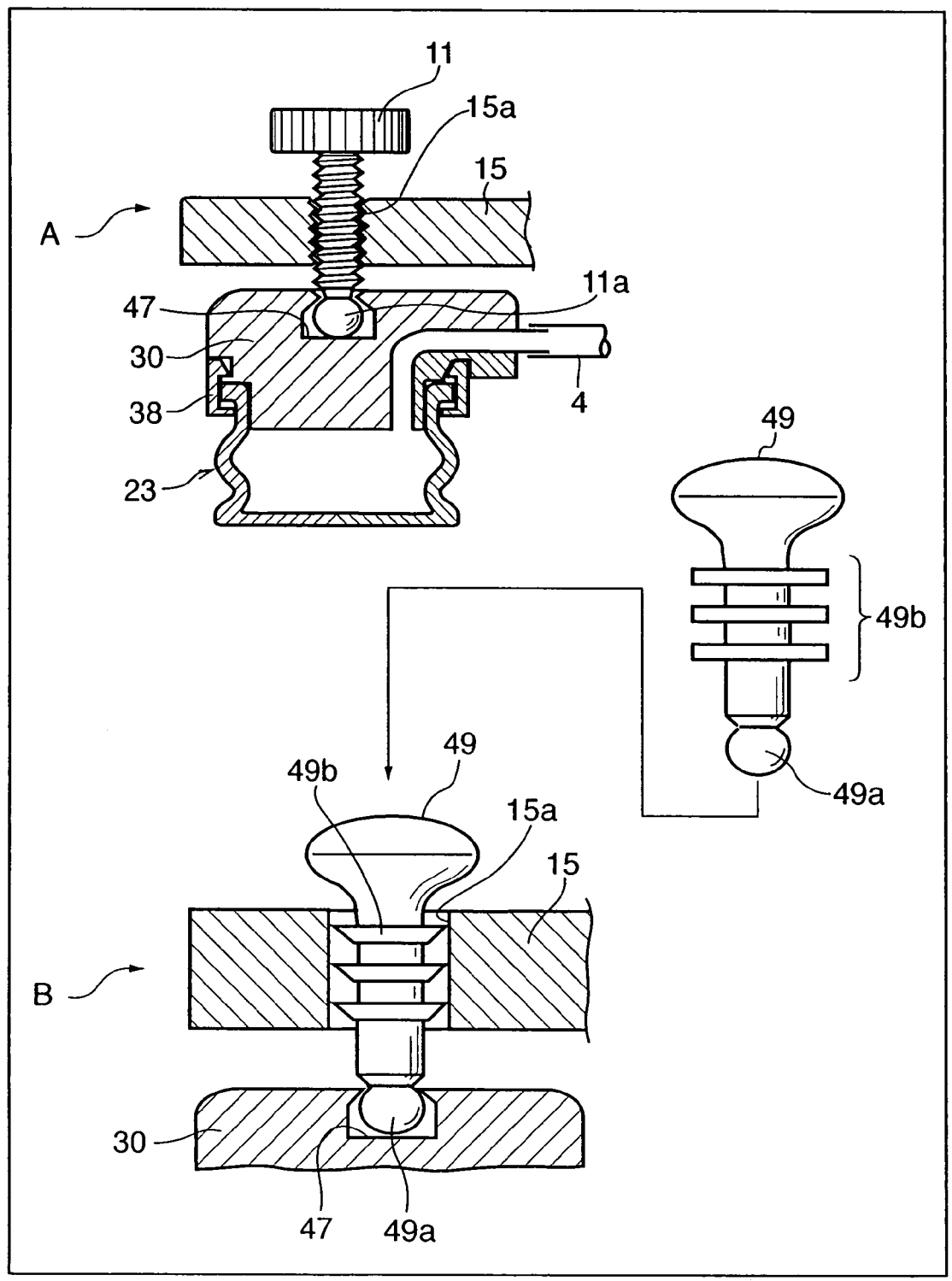
Figure 19:
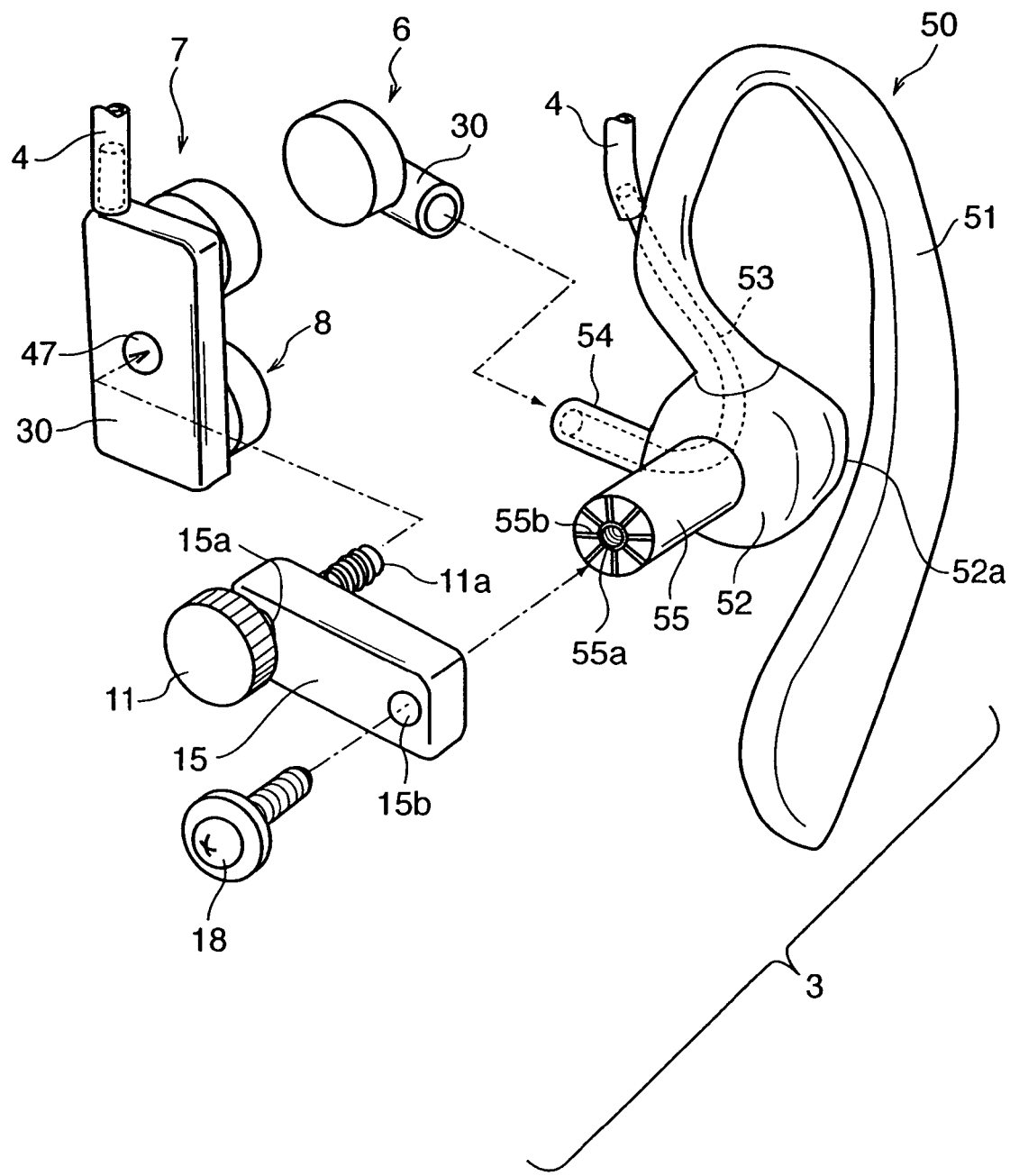
Figure 20:
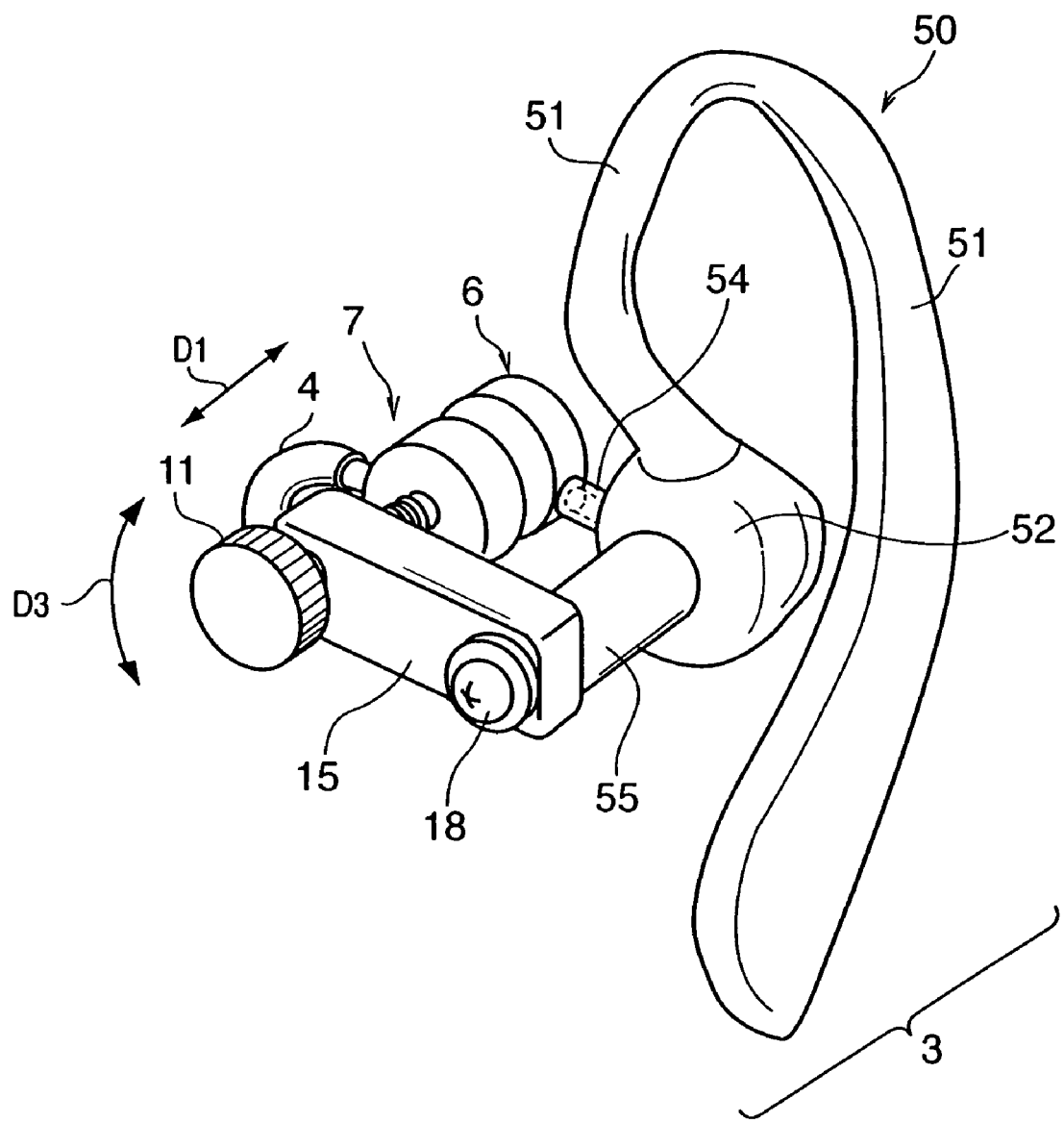
Figure 21:
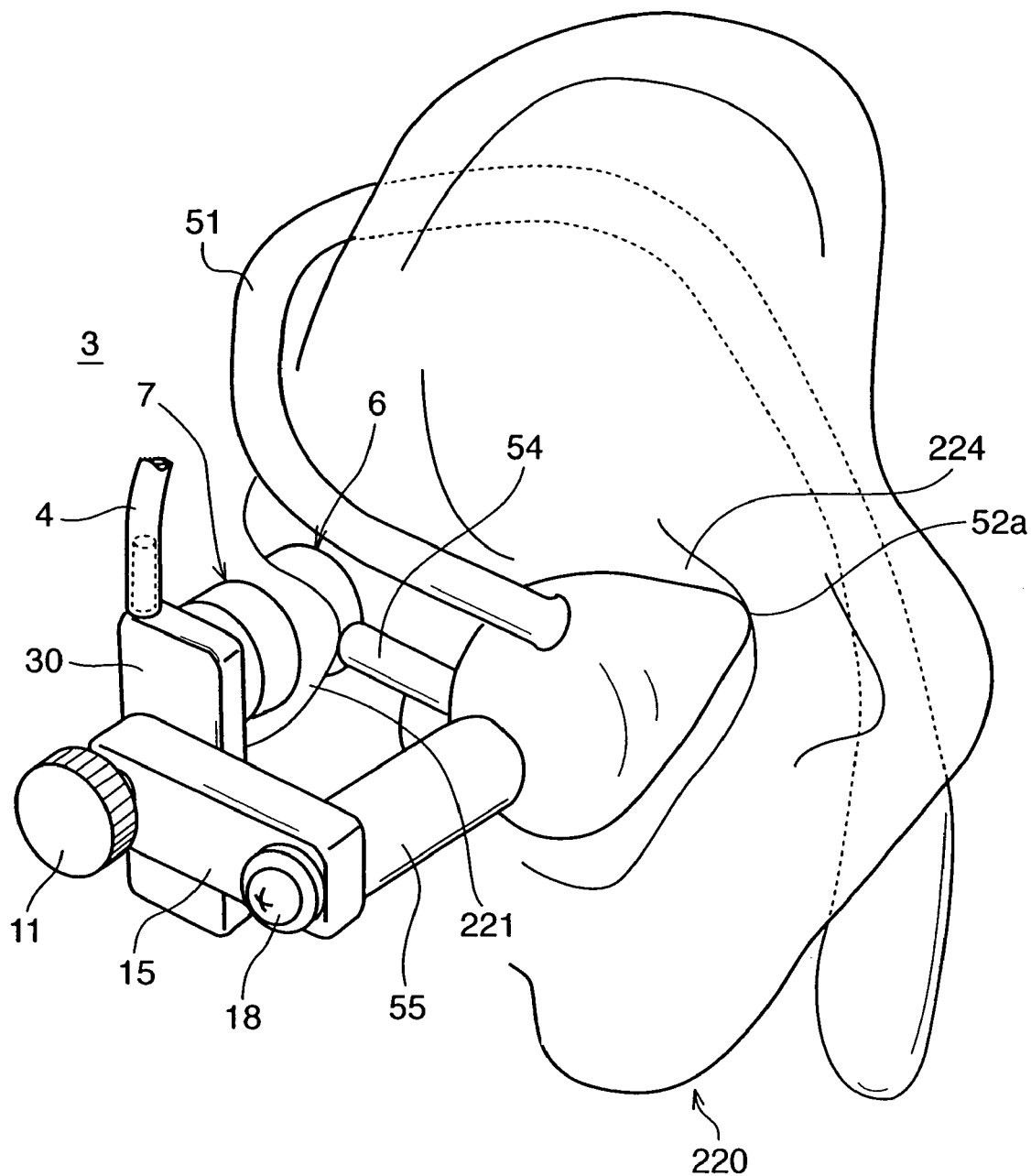
Figure 22:
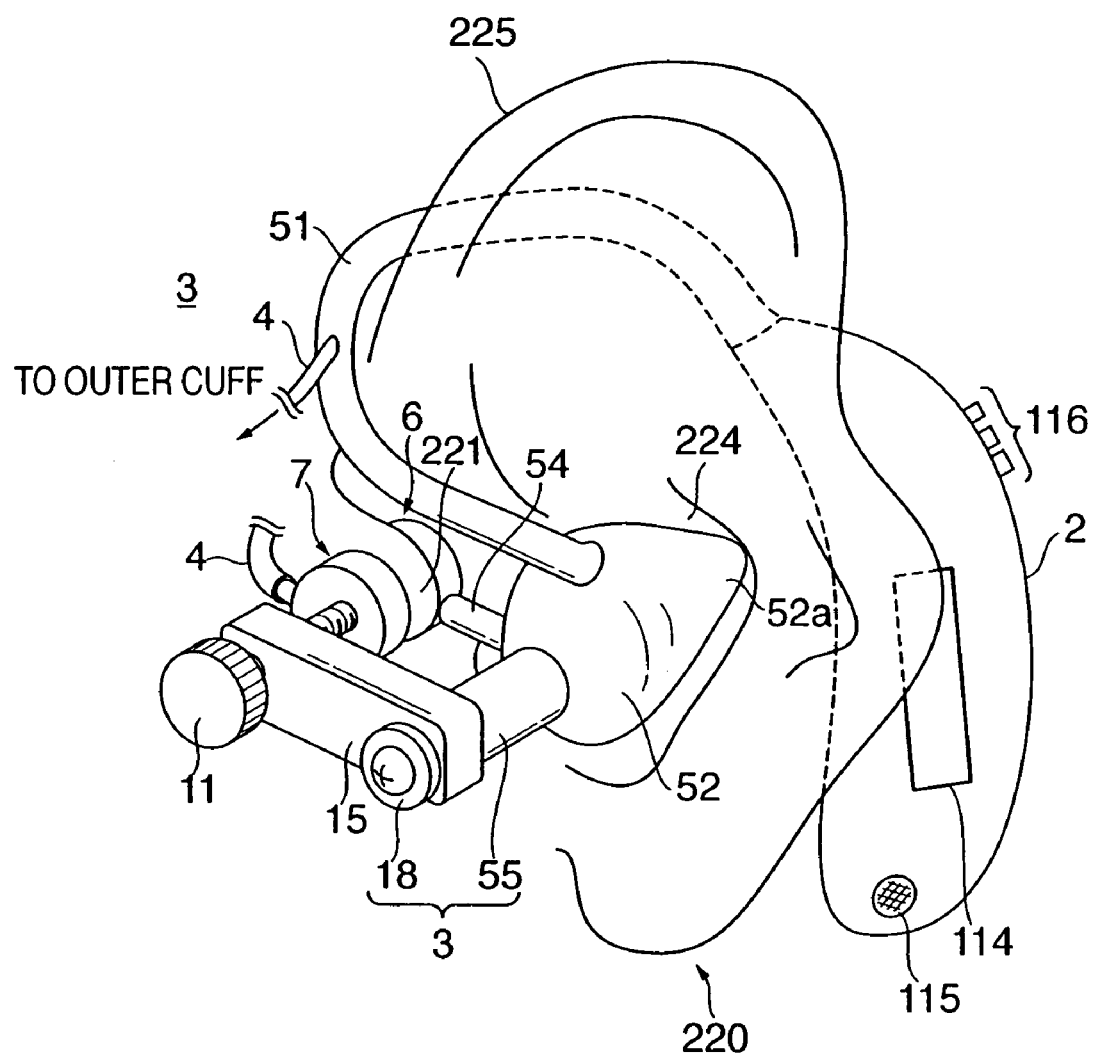
Figure 23:
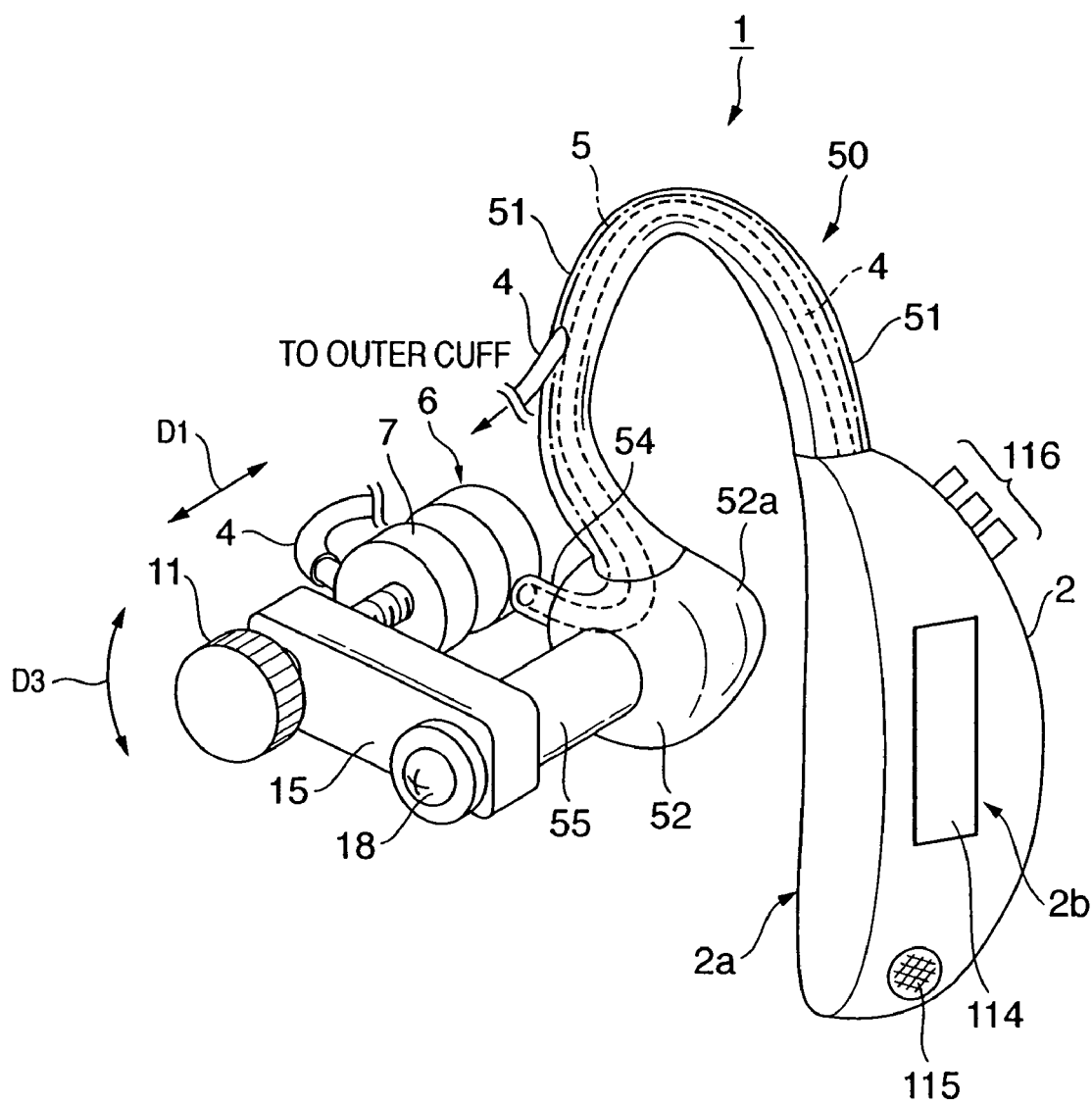
Figure 24:
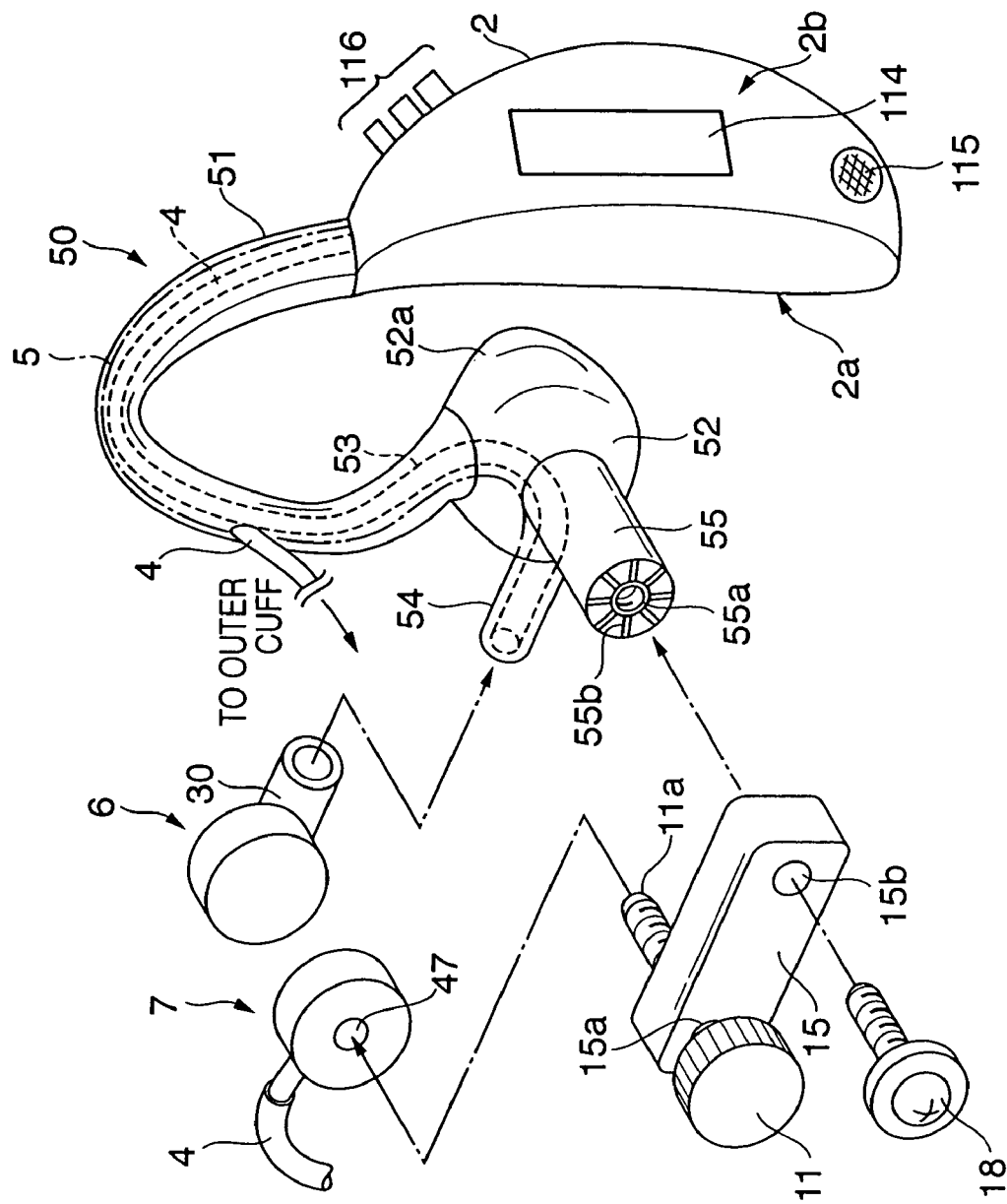
Figure 25:
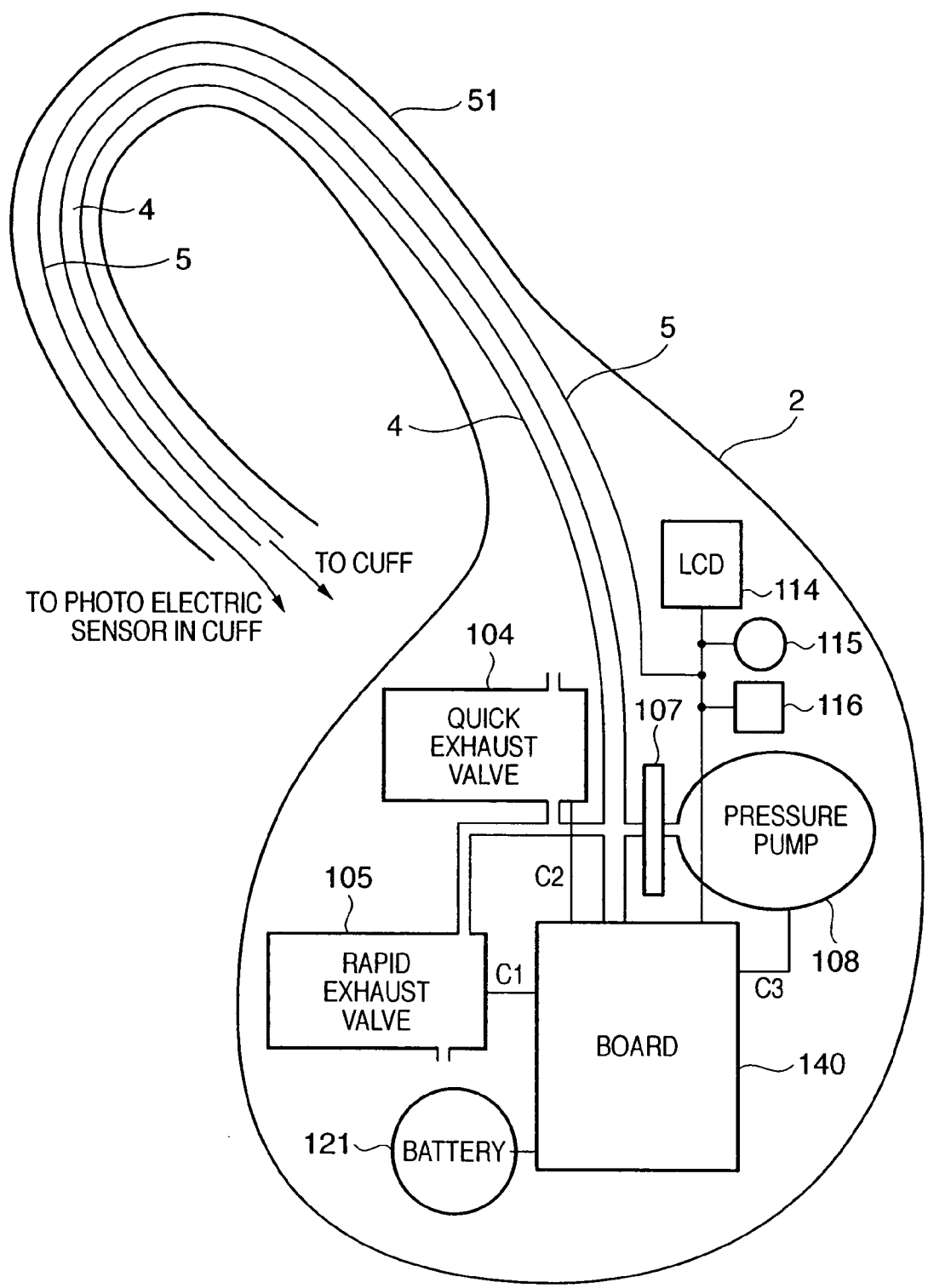

A of FIG. 6 is a sectional view showing another arrangement of the embodiment for the blood pressure measuring apparatus 1, B of FIG. 6 is an outer appearance perspective view of A of FIG. 6;

A of FIG. 7 is a sectional view after attaching the support portion 3 of the blood pressure measuring apparatus 1 to the tragus shown in FIG. 1, B of FIG. 7 is a perspective view of A, and C of FIG. 7 is a bottom view;

FIG. 8 is a sectional view taken along a line X-X in A of FIG. 7;

A of FIG. 9 is a plan view of a cuff bladder 22, 23, B of FIG. 9 is a front view of the cuff bladder, C of FIG. 9 is a right side view of the cuff bladder, and D of FIG. 9 is a bottom view of the cuff bladder;

A of FIG. 10 is a sectional view of cuff bladder 22,33, B of FIG. 10 is a sectional view of the cuff bladder;

FIG. 11 is a block diagram showing an example of the configuration of a blood pressure measuring apparatus 1 according to another embodiment;

FIG. 12 is a waveform diagram showing the results of blood pressure measurement performed by simultaneous measurement by the inner and outer cuffs;

A of FIG. 13 is an exploded sectional view showing the state in which the cuff bladder is attached to the cuff member, B of FIG. 13 is a sectional view showing a portion of the cuff assembly after being assembled;

FIG. 14 is a sectional view showing another embodiment of the cuff assembly;

FIG. 15 is an outer appearance perspective view showing how cables and a tube are integrated;

A of FIG. 16 is a sectional view showing the cuff assembly that is not light shielded, B of FIG. 16 is a sectional view showing the cuff assembly that is light shielded;

FIG. 17 is a view showing printing steps of forming a light-shielding layer in the interior of the cuff bladder 22, together with the central sectional views of the cuff bladder 22;

A of FIG. 18 is a sectional view showing that the cuff assembly is provided at the distal end of the adjustment screw 11 mounted on the third support member 15 with some degree of freedom, B of FIG. 18 is a sectional view showing that the cuff assembly is provided at the distal end of the one-way moving member or brushing member;

FIG. 19 is an exploded isometric view of the installation portion 3;

FIG. 20 is a perspective view of the installation portion 3 after assembly is completed;

FIG. 21 is a perspective view showing the state how the installation portion 3 is used;

FIG. 22 is a perspective view showing the state that the installation portion 3 of the blood pressure measuring apparatus 1 is mounted onto the tragus 221;

FIG. 23 is a perspective view of the installation portion;

FIG. 24 is an exploded isometric view of the installation portion 3;

FIG. 25 is a view showing the layout of parts of an apparatus main body 2, wherein the lid is detached from the main body.

BEST MODE FOR CARRYING OUT THE INVENTION

First of all, the most important feature of this invention is to use the tragus as a blood pressure measurement point. The reason for choosing the tragus as a measurement point for blood pressure measurement is because the tragus is one portion of the auricle and is very small, thus providing the advantage that a blood pressure detecting element can be miniaturized. Moreover, because the tragus is one part of the head, the positional change with respect to other body portions is small, making it suitable for blood pressure measurement. In addition, because the tragus is not used for purposes other than for collecting sonic reflection, it is enumerated to be able to reduce the degree of invasion by which pain is imposed on the patient when the blood pressure is measured. Therefore, the obstacle to daily life can be made fewer than when on the finger, etc., even if the cuff is always installed. In addition the blood pressure detecting element can be made miniaturized.

The reason why the pain given to the patient is reduced when the tragus is used as the blood pressure measurement point is added is as follows: because the brachium and the finger do complex work as a part of the human body, a lot of nerves surrounding blood vessels for the brachium and the finger exist here. On the other hand, the tragus, being one portion of the head, is fixed to the head, and is not used for purposes other than for collecting sonic reflection, the amount of the nerves around the ear is less than that of the arm and the finger. Therefore, when the blood pressure is measured by making the tragus as a blood pressure measurement point, there are advantages that the pain is reduced compared with the blood pressure measurement that uses the brachium and the finger, and cuffs can be made small as well.

However, because the tragus is one portion of the auricle and is very small, if a small blood pressure measurement device is not attached to tragus properly and immovably, accurate measurement of blood pressure becomes impossible.

The blood pressure detecting device is usually connected with wiring which is the signal wire of the output signal, etc., transmitted from the electric power. The device is also connected with the piping to supply the pressurizing fluid or air under pressure to pressurize the tragus and the blood pressure detecting element. This piping and wiring is connected to the main body of the blood pressure measurement device. For this, when the blood pressure is measured for a long period of time, the position where the blood pressure detecting element is installed shifts because the main body of the blood pressure measurement device is moved by touching of piping and wiring with the hands, and correct blood pressure measurement becomes impossible.

A blood pressure measuring apparatus of a preferred embodiment according to the present invention will be explained below with reference to the accompanying drawings. The following forms and sizes of the blood pressure measurement apparatus are merely examples of this invention, and it is needless to say that the scope of this invention is limited by them.

<Whole Arrangement>

FIG. 1 is an outer appearance perspective view showing the state in which the blood pressure measuring apparatus 1 according to the present invention is used for the auricle.

By referring to FIG. 1, the auricle 220 or so called ear has the tragus 221, the antitragus 222, the auricular concha 223, the antihelix 224, the helix 225, the antihelix crura 226 and the ear hole 230, each having mutual positional relations as shown. Moreover, extended portions (not shown in the figure) containing the cartilage constituting an ear hook mounting part of the apparatus is formed on the head side portion on the backside of the antihelix 224. As for shape and size of each of these parts, it is known that sex, age or individual differences according to race is large. Moreover, it is known that the shallow head side artery is vertically built-in beside the tragus 221.

Next, this ear type blood pressure measuring apparatus 1 is composed of an inner cuff assembly body 6 which is inserted into the ear hole 230 for providing one of the cuffs, an installation part 3 on which an outer cuff assembly body 7 for providing another cuff is supported by a support member 10 as shown, and a main body device 2 connected through piping 4 and wiring 5 from the installation part 3. Moreover, the outer cuff assembly body 7 is fixed at a distal end of a clamping width adjustment screw 11 for adjusting a clamping width size via a ball type bearing (not shown in the Figure), so that the outer cuff assembly body 7 can wobble freely and can evenly touch the tragus 221.

The main body 2 of the device is accommodated for instance in a breast pocket or a special porch of the patient while an installation part 3 is set in the tragus 221 of a left ear as shown. The installation part 3 can be set in a right ear as well. Moreover, after the main body 2 of the device is put in the breast pocket of clothes by using the clip, etc., it becomes possible to prevent the device from dropping out in daily life movement. Moreover, by arranging the liquid crystal display part and the start switch, etc., on the main body 2 of the device, it may become possible to do necessary operations for measuring the blood pressure without taking the device out of the pocket.

<Circuit Configuration of Photoelectric Volume Pulse Wave Blood Pressure Measuring Apparatus>

Figure 2:
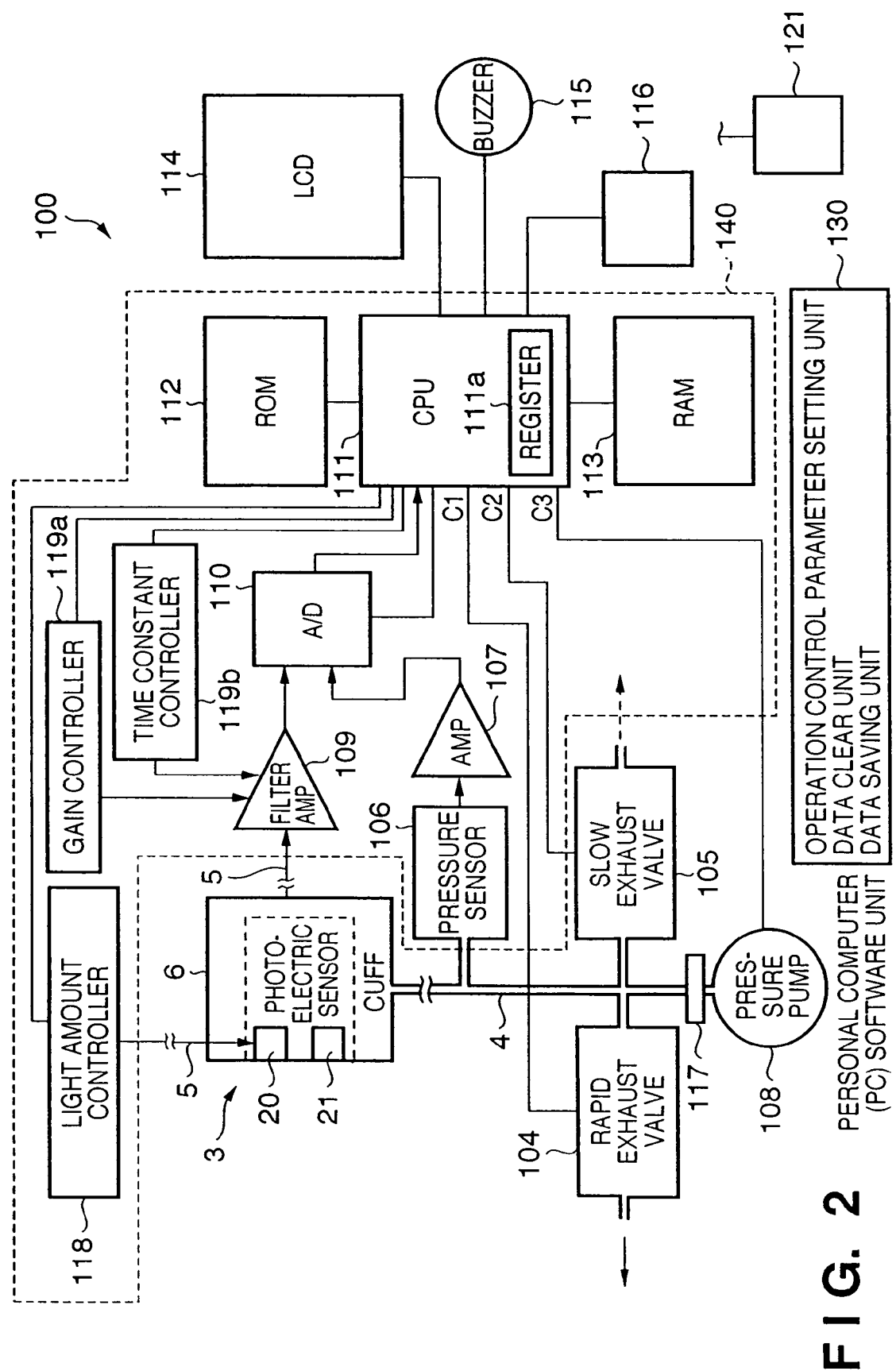
FIG. 2 is a block diagram showing an example of the configuration of the blood pressure measuring apparatus 1 shown in FIG. 1.

FIG. 2 is a block diagram showing the configuration of an operating circuit 100 in the apparatus main body 2 when the blood pressure measuring apparatus 1 is constructed as a photoelectric volume pulse wave blood pressure measuring apparatus. Referring to FIG. 2, the inner cuff (assembly) 6 of the installation part 3 to be attached to the tragus 221 incorporates the LED 20 as a light-emitting element and the phototransistor 21 as a light-receiving element forming a photoelectric sensor (pulse wave sensor). The above described tube 4 is a rubber tube (air tube), and forms an air channel to the inner cuff 6. A pressure pump 108 has a small electric motor as a driving source, supplies compressed air to a condenser tank 117, and supplies pressurized air into the inner cuff assembly 6 after rectification. A rapid exhaust valve 104 branched from the tube 4 has a solenoid valve mechanism (not shown), and rapidly reduces the internal pressure of the inner cuff assembly 6. A slow exhaust valve 105 that is similarly branched reduces the internal pressure of the inner cuff assembly 6 at a predetermined rate (e.g., 2 to 3 mmHg/sec). Also, a pressure sensor 106 branched from the tube 4 changes an electrical parameter in accordance with the internal pressure of the cuff 6. A pressure detection amplifier (AMP) 107 connected to the pressure sensor 106 detects the electrical parameter of the pressure sensor 106, converts the parameter into an electrical signal, and amplifies the signal, thereby outputting an analog cuff pressure signal P.

The LED 20 irradiates a pulsing blood flow with light, and the phototransistor 21 detects the reflected light from the blood flow. A filter AMP 109 connected by the cables 5 is a pulse wave detection amplifier, and outputs an analog pulse wave signal M by amplifying the output signal from the phototransistor 21. The cables 5 connect the LED 20 to a light amount controller 118 that automatically changes the amount of light, and connect the pulse wave detection amplifier 109 to a gain controller 119a that automatically changes the gain, and a time constant controller 119b that changes the time constant of a filter amplifier (not shown) forming the pulse wave detection filter amplifier 109. Also, an A/D converter (A/D) 110 connected as shown in FIG. 20 converts the analog signals M and P into digital data D.

A controller (CPU) 111 performs main control of the photoelectric volume pulse wave blood pressure measuring apparatus. The CPU 111 has an adjusted pressure register 111a that stores an adjusted pressure. Details of this control will be explained later with reference to flowcharts shown in FIGS. 4A and 4B and an operating waveform diagram shown in FIG. 5.

A ROM 112 contains a control program (to be described later) executed by the CPU 111. A RAM 113 includes a data memory, image memory, and the like. A liquid crystal display (LCD) 114 displays the contents of the image memory. An operation unit 116 is operated by the user to, for example, input a measurement start command or set an adjusted pressure value. A buzzer 115 notifies the user that, for example, the apparatus has sensed pressing of a key in the operation unit 116, or the measurement is complete. Note that the adjusted pressure register 111a is allocated in the CPU 111 in this embodiment, but an adjusted pressure storage unit may also be allocated in the RAM 113.

A dot matrix type display panel is used as the display panel 114 of the LCD, so the display panel 114 can display various kinds of information (e.g., characters, figures, and signal waveforms). The operation panel 116 has a measurement start switch (ST) and keys for inputting, for example, a cuff pressure value. The apparatus further includes a power supply unit 121 having an exchangeable battery, and a power switch (not shown).

Furthermore, the apparatus main body 2 has an external communication unit to be connected to a connector or cell phone (neither is shown). By connecting this external communication unit to a personal computer, it is possible to exchange various kinds of data with and save the blood pressure measurement results in an operation control parameter setting unit, data clear unit, and data saving unit of the personal computer.

Figure 3:
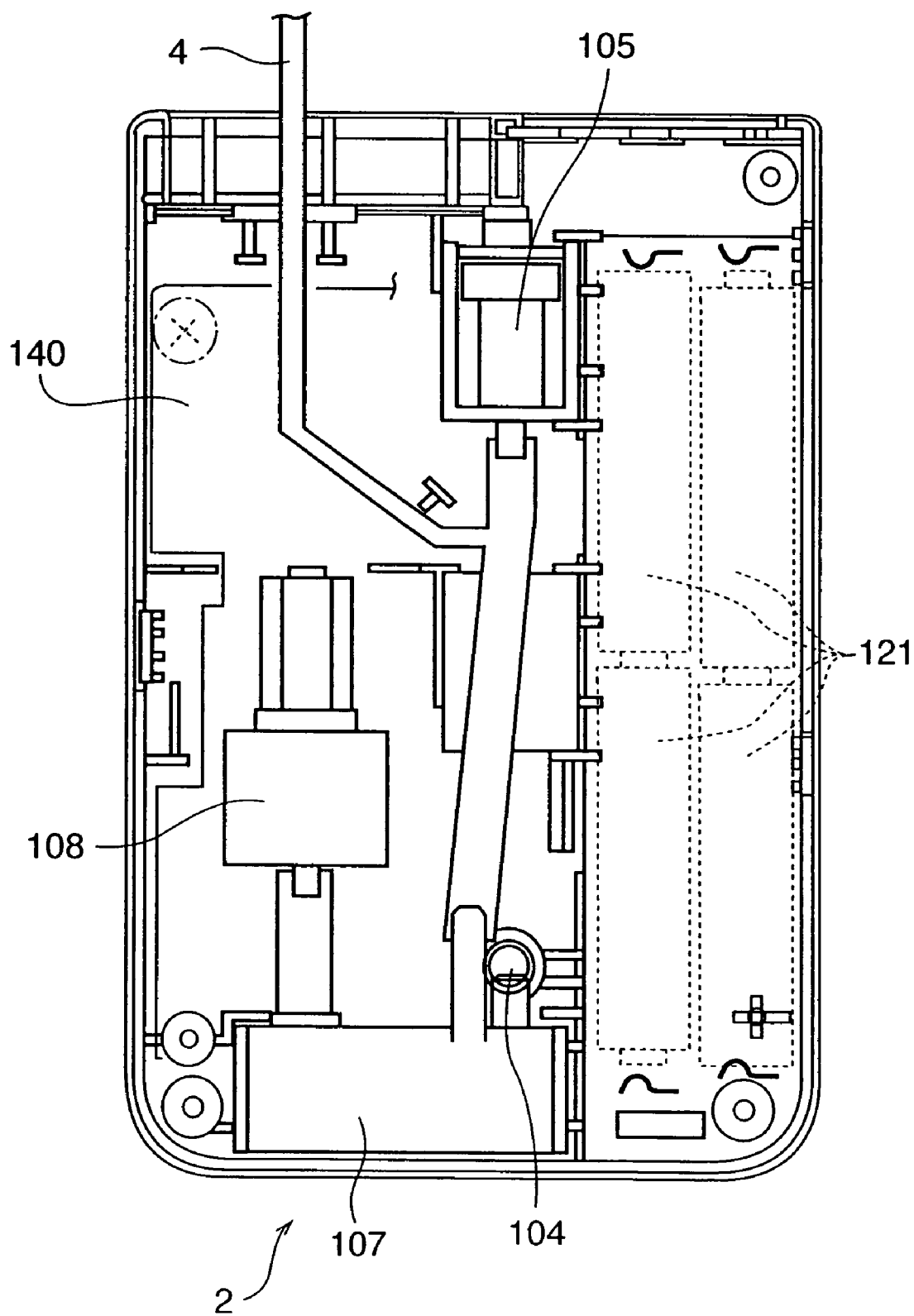
FIG. 3 is a view showing the layout of parts of an apparatus main body 2 shown in FIG. 1.

FIG. 3 is a view showing the layout of the parts of the apparatus main body 2 shown in FIG. 2, in which the lid is removed from the apparatus main body 2. In FIG. 3, the same reference numerals as above denote the already explained arrangements or parts, and a repetitive explanation will be omitted. The apparatus main body 2 has a length of about 120 mm, a width of about 80 mm, a thickness of 27 mm, and an overall weight of 180 g. Since the apparatus main body 2 is thus made as compact and light as possible, it does not interfere with everyday life even when the user always carries it.

Also, the electronic parts that perform the various kinds of control described above are mounted on a substrate 140 having a packaging area that occupies the internal space. On the other hand, the pressure pump 108, condenser tank 107, slow exhaust valve 105, and rapid exhaust valve 104 are connected to the tube 4 that is formed integrally with these components as described above, and have the relative positional relationship as shown in FIG. 21, so these components can be installed together with the power supply unit 121 containing four exchangeable AAA cells. The electronic parts are thus arranged such that the limited internal space can be effectively used. In addition, a chargeable secondary battery that can be repetitively used or commercially available AAA cells that are readily obtainable can be simply exchanged by opening and closing a lid (not shown).

<Operation of Photoelectric Volume Pulse Wave Blood Pressure Measuring Apparatus>

Figure 4A:
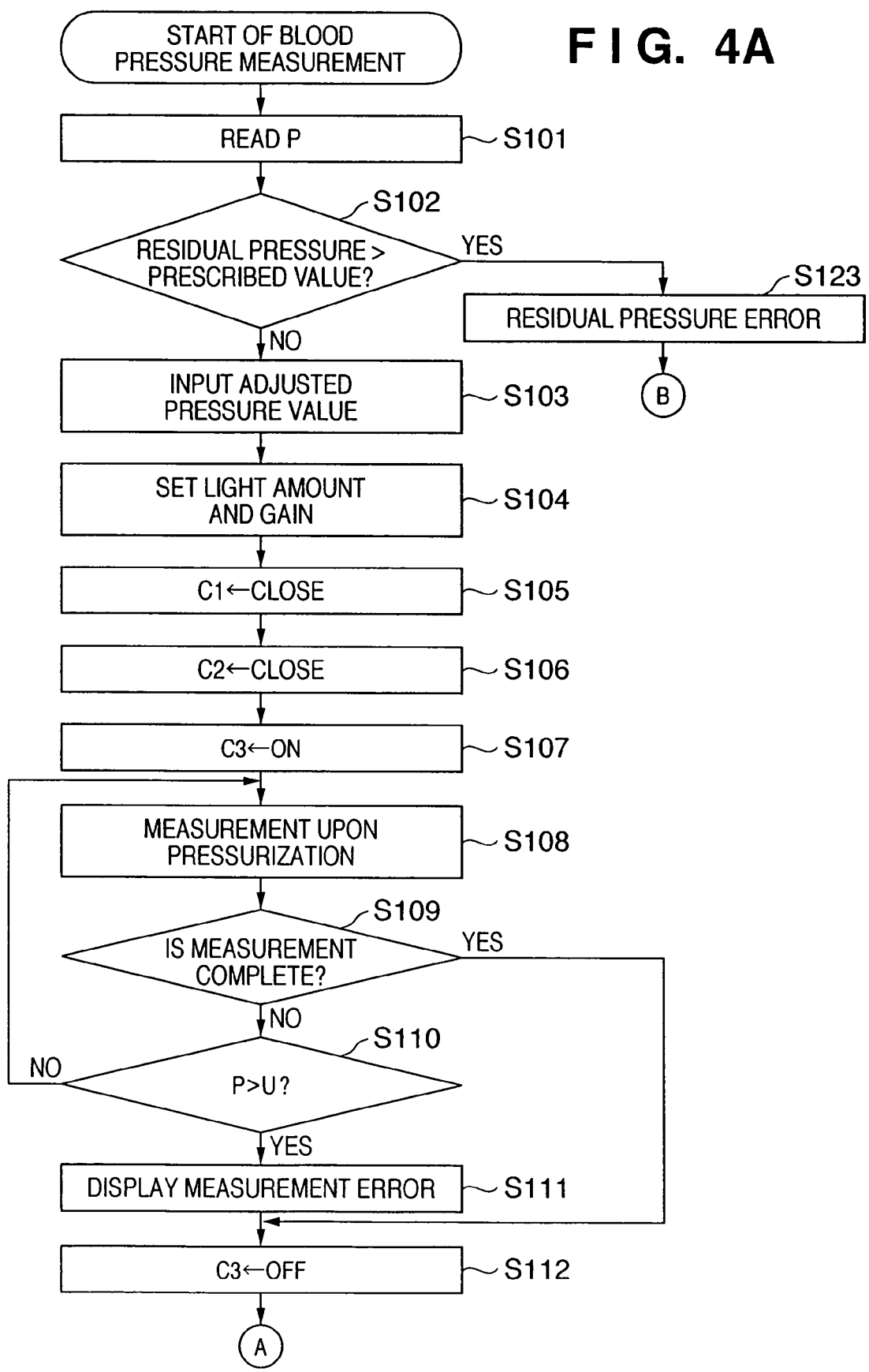
FIG. 4A is a flowchart for explaining the operation of the blood pressure measuring apparatus 1.
Figure 4B:
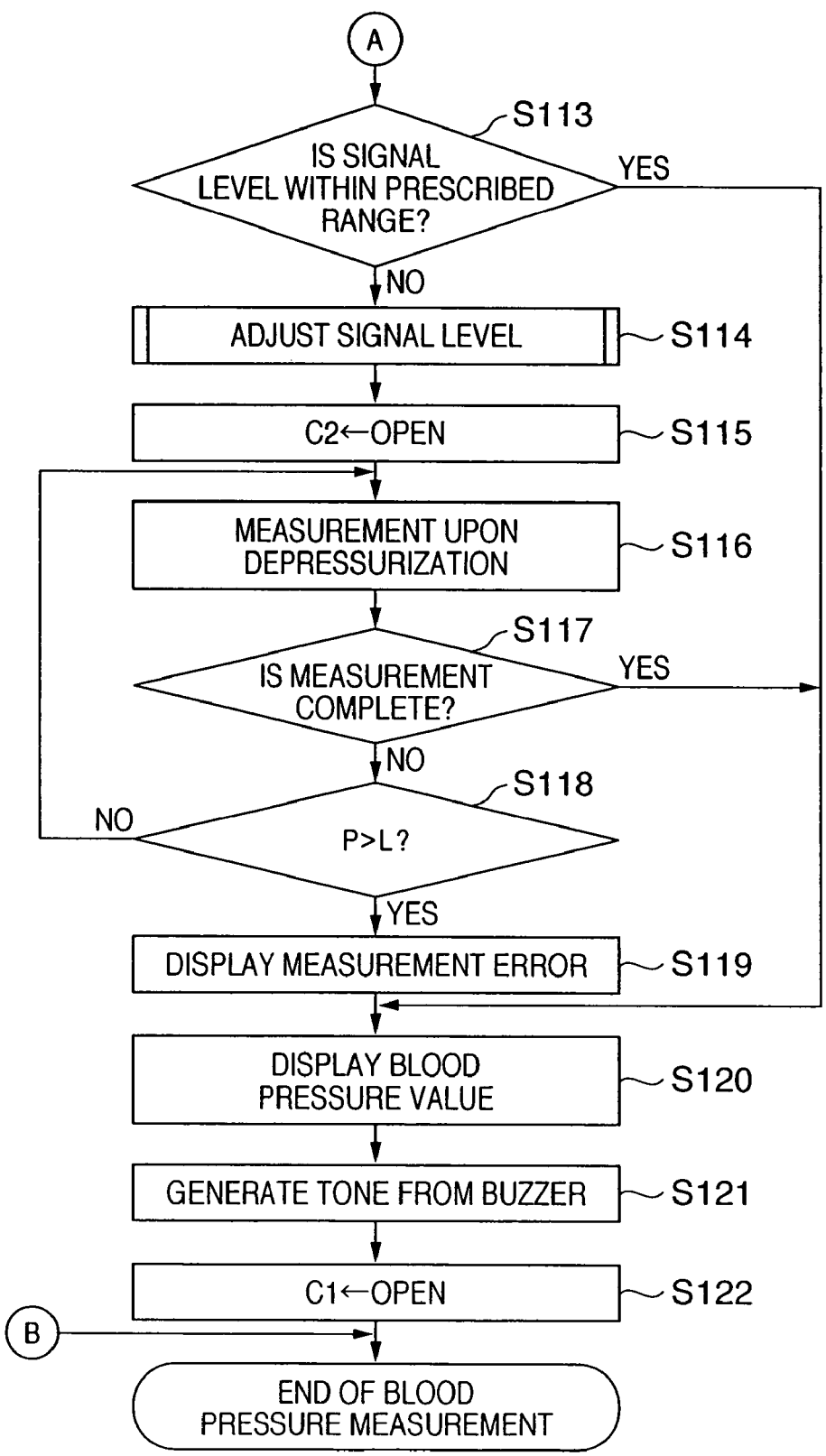
FIG. 4B is a flowchart for explaining the operation of the blood pressure measuring apparatus 1.

The operation of the blood pressure measuring apparatus according to this embodiment as a photoelectric volume pulse wave blood pressure measuring apparatus, an ear type blood pressure measuring apparatus, will be explained below. FIGS. 4A and 4B are flowcharts for explaining the measurement process of the blood pressure measuring apparatus (photoelectric volume pulse wave blood pressure measuring apparatus). Referring to FIGS. 4A and 4B, when the user turns on the power supply by the power switch of the apparatus, an initial self-diagnosing process (not shown) is first performed to set the initial values of the apparatus. After that, the process is started when the user presses the measurement start switch.

The cuff pressure P is read in step S101, and whether the residual pressure of a cuff 6 is equal to or smaller than a prescribed value is determined in step S102. If the residual pressure exceeds the prescribed value, the LCD 114 displays "residual pressure error" in step S123. If the residual pressure is equal to or smaller than the prescribed value, the user sets a cuff pressurization value (e.g., a value larger than a maximum blood pressure value of 120 to 210 mmHg) in step S103 by using the operation unit 118, and sets the light amount and gain at predetermined values in step S104.

After the pressurization value, light amount, and gain are set, the rapid exhaust valve 104 and slow exhaust valve 105 are closed in steps S105 and S106. In step S107, the pressure pump 3 is driven to start pressurization (raising the pressure). This is the start of a measurement process upon pressurization, and the cuff pressure starts increasing at a constant rate (e.g., 2 to 3 mmHg/sec). In step S108, the individual functional blocks perform data processing, and measure the minimum blood pressure and maximum blood pressure. When the maximum blood pressure is measured (S109), the driving of the pressure pump 108 is stopped in step S112.

In step S110, it is determined whether the cuff pressure is higher than a pressurization value U set in step S103. If P<U, the cuff pressure still falls within a normal measurement range, so the measurement continues. If P>U, the cuff pressure is higher than the set value, so the LCD 114 displays "measurement error" in step S111. If necessary, the LCD 114 additionally displays detailed information such as "signal abnormality upon pressurization". In step S113, it is determined whether the signal level of a pulse wave signal obtained upon pressurization falls within a predetermined range over which highly accurate blood pressure measurement is possible. If the signal level falls within the predetermined range, the LCD 114 displays the measured maximum blood pressure value and minimum blood pressure value in step S120, and a tone signal is supplied to the buzzer 115 in step S121.

If the signal level falls outside the predetermined range in step S113, the light amount and gain are adjusted based on the signal level of the pulse wave signal in step S114. In step S114, the apparatus performs, for example, the following processing. If the carrier wave of the pulse wave is equal to or smaller than a standard value (20% to 40% of the full scale of the A/D converter 110), whether the step light amount is a maximum is checked. If the step light amount is not a maximum, the light amount is increased by controlling the light amount controller 118. If the light amount is a maximum, the gain is raised. On the other hand, if the carrier wave level is equal to or larger than the standard value, whether the gain is a minimum is checked. If the gain is not a minimum, the gain controller 119a lowers the gain by feedback control. If the gain is a minimum, the light amount is decreased.

When the adjustment of the light amount and gain is complete, the slow exhaust valve 105 is opened in step S115. This is the start of a measurement process upon depressurization (pressure reduction), and the cuff pressure starts reducing at a constant rate (e.g., 2 to 3 mmHg/sec). In step S116, the individual functional blocks perform data processing, and measure the maximum blood pressure and minimum blood pressure. In step S117, whether the minimum blood pressure value is detected upon depressurization is determined. If no value is detected, the measurement continues. In step S118, whether the cuff pressure is lower than a predetermined value L (e.g., 40 mmHg) is determined. If P≧L, the cuff pressure still falls within the normal measurement range, so the process returns to step S116. If P<L, the cuff pressure is lower than the normal measurement range, so the LCD 114 displays "measurement error" in step S119. If necessary, the LCD 114 additionally displays detailed information such as "signal abnormality upon depressurization".

If it is determined in step S117 that the measurement is complete, this means that the measurement process is complete within the normal measurement range. Accordingly, the LCD 114 displays the measured maximum blood pressure value and minimum blood pressure value in step S120, and a tone signal is supplied to the buzzer 115 in step S121. Preferably, different tone signals are supplied for normal termination and abnormal termination. In step S122, the remaining air in the cuff 6 is rapidly exhausted, and the start of the next measurement is awaited.

<Blood Pressure Calculations>

Figure 5:
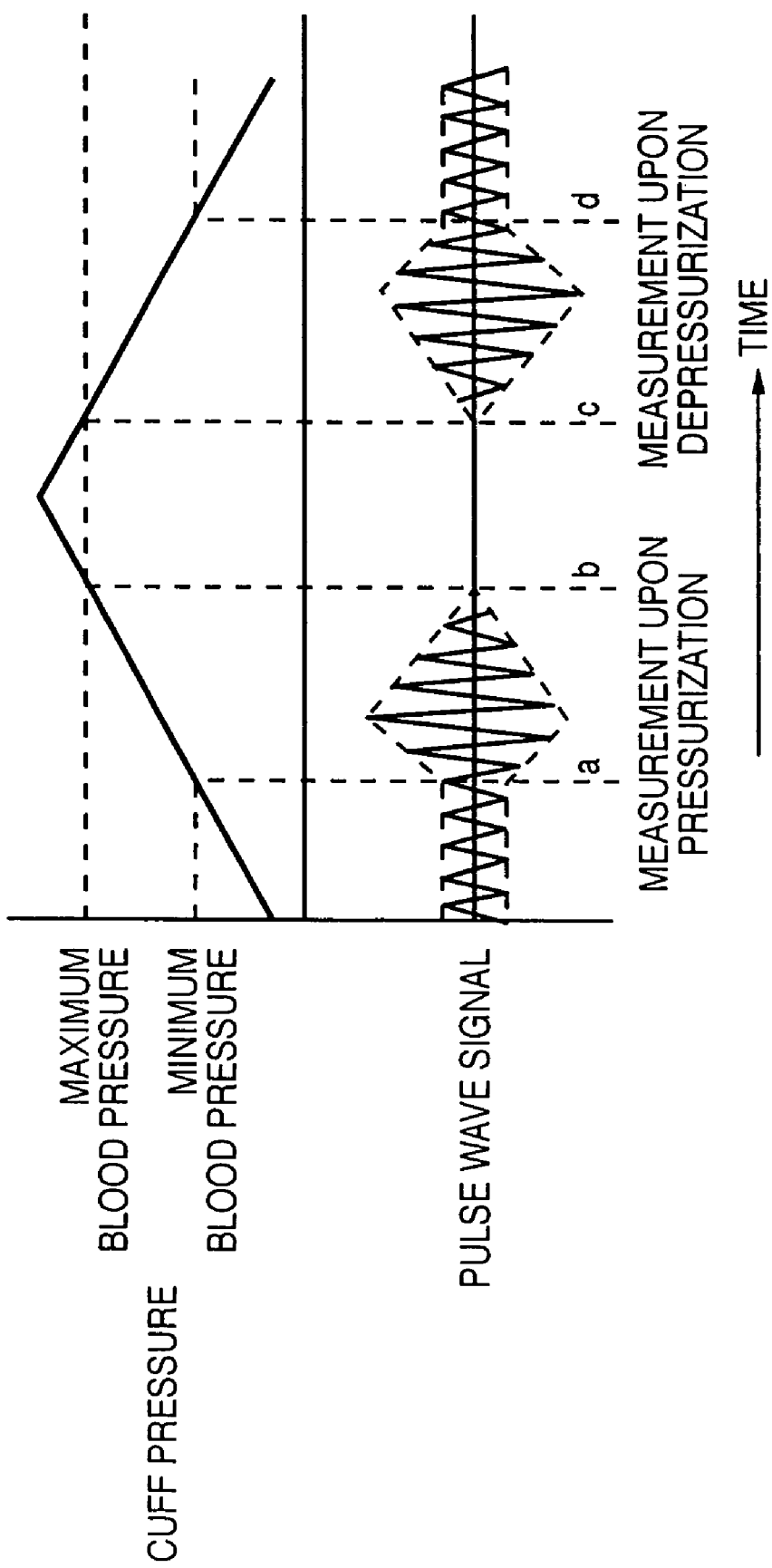
FIG. 5 is a waveform diagram of blood pressure measurement.

FIG. 5 is a graph showing the correlation between the cuff pressure and pulse wave signal. FIG. 5 shows waveforms during a time period from the start of the measurement upon pressurization (step S108) to the end of the measurement upon depressurization (step S116).

Referring to FIG. 5, blood pressure measurements are generally performed as follows. That is, in the measurement upon pressurization, the cuff pressure at the point (a) at which the pulse wave signal starts changing its magnitude is the minimum blood pressure, and the cuff pressure at the point (b) at which the pulse wave signal disappears is the maximum blood pressure. On the other hand, the blood pressure measurement upon depressurization is opposite to that upon pressurization; the cuff pressure at the point (c) at which the pulse wave signal appears is the maximum blood pressure, and the cuff pressure at the point (d) at which the pulse wave signal stops changing its magnitude is the minimum blood pressure.

Note that this embodiment has disclosed an example in which the reflected light from the blood in the blood vessel is detected, but it is also possible to detect transmitted light instead.

As explained above, the photoelectric volume pulse wave blood pressure measuring apparatus of this embodiment makes it possible to provide a photoelectric volume pulse wave blood pressure measuring apparatus capable of highly accurate measurement by adjusting the signal level of a pulse wave signal such that the signal level falls within a predetermined standard range, and also capable of reducing the physical burden on the user caused by the cuff pressure by shortening the blood pressure measurement time. Note that the tragus and its periphery are less sensitive to pain, so it is also possible to effectively reduce the pain caused by the cuff pressure. This further achieves the effect of facilitating the application of the apparatus to continuous blood pressure measurement.

Note that the above blood pressure measuring apparatus detects the pulse wave by using the light-emitting element 20 and light-receiving element 21, but it is also possible to detect the pulse wave by sensing the pulsation (oscillation) of the blood vessel on the surface of a living body as a pressure change by using a cuff that applies pressure to the tragus. That is, a cuff to which pressure is applied converts the pulsation obtained from a living body into a pressure change in the cuff, and a pressure sensor senses this pressure change in the cuff. This arrangement can also detect the pulse wave of a living body. It is also possible to install a miniature microphone in a cuff portion in contact with a living body, detect Korotkoff sounds generated when the cuff presses a portion of the living body, and measure the blood pressure based on the generation or disappearance of Korotkoff sounds equal to or higher than a predetermined level.

<Arrangement of Supporting Means for Inner and Outer Cuffs>

Next, A of FIG. 6 is a sectional view showing an installation part 3 of the ear type blood pressure measuring apparatus 1 shown in FIG. 1 after the installation part 3 is installed to the tragus, and B of FIG. 6 is an outer appearance perspective view of A of FIG. 6. In the figures the same reference numerals as above denote the already explained arrangements or parts, and a repetitive explanation will be omitted. The inner cuff assembly body 6 to be inserted into the ear hole that is located inside the tragus incorporates the above-mentioned LED 20 and photo transistor 21, and a cuff bladder 22 which is fixed using an O ring 24 at a distal end portion of the first support member 13 having a channel 4a which leads to the piping 4. Moreover, the outer cuff assembly body 7 located outside portion of the tragus comprises a cuff bladder 23 that is fixed to a member using the O ring 24. The member is connected to the flexible piping 4b that is connected to a T branch tube 12. Each of these cuff bladders 22 and 23 has basically the same configuration, and an oval configuration can be used besides the circle as will be described later. Each of these cuff bladders 22 and 23 are made of silicon rubber and made airtight as shown in the Figure.

On the other hand, this first support member 13 has an extended portion formed squarely as shown, and a second support member 14 is attached at the distal end of the extended portion through a second adjustment screw 19 so that the second support member can be rotated and fixed to be immovable after the adjustment. Moreover, a third support member 15 is attached to the second support member 14 using a first adjustment screw 18 and a spacer 17, so that the third support member can be rotated and fixed to be immovable after the adjustment.

As for the above-mentioned inner cuff assembly body 7, it is installed with a clamping width controlling element or a clamping width adjustment screw 11 that has a ball bearing portion 11a on the distal end as shown, so that the inner cuff assembly body 7 can do free neck moving operations.

In B of FIG. 6, according to the above-mentioned arrangement, the inside cuff assembly body 6 is first inserted into the ear hole, the second adjustment screw 19 is loosened with a tool such as a precision plus driver, etc., the second support member 14 is moved in the direction of arrow D2 shown in the figure so that the tragus is pinched between the inside cuff assembly body 6 and the outer cuff assembly bodies 7, and finally the second adjustment screw 19 is tightened and fixed to an immovable state.

After this, the first adjustment screw 18 is similarly loosened, the third support member 15 is turned with respect to the second support member 14 in the direction of arrow D3 as shown in the figure so that the outer cuff assembly body 7 opposes the inside cuff assembly body 6 as much as possible, and the first adjustment screw 18 is tightened to put them into an immovable state. finally, the clamping width adjustment screw 11 is turned in a positive direction or the opposite direction such that a clamping width is optimal and the adjustment is finished.

Since the outer cuff assembly body 7 is supported by the ball bearing portion, it can move in three dimensions with a wobbling movement, and it becomes possible to surely pinch the tragus 221 that has great individual differences. Moreover, the cuff bladders 22 and 23 are made to inflate when air or pneumatic pressure is sent from a pressure pump 108 via a condenser tank 117, and deflate when depressed and repeat these operations.

Here, in order to use the tragus as a blood measuring point to perform accurate measurement, in addition to above mentioned function of inflating and deflating, the cuff bladders 22 and 23 must have another function of being able to flatly make contact with the surface of the tragus, and of being able to maintain the state that the inner cuff and outer cuff oppose each other. Although maintaining the state that the inner cuff and outer cuff oppose each other was realized with a three-dimensional wobbling movement, it was found to be difficult to keep both the inner cuff and outer cuff contact state evenly with respect to the inside and outside surface of the tragus.

Accordingly, inventors confirmed that the following shape was best through trial and error of shape such that cuff bladders 22 and 23 were able to come into contact flatly with respect to the inside and outside of the tragus.

<Arrangements of Cuff Bladders 22 and 23>

A of FIG. 7 is a plan view of the cuff bladders 22, 23 forming a part of the cuff assemblies, B of FIG. 7 is a front view of the cuff bladder 22, and C of FIG. 7 is a bottom view of the cuff bladder 22. FIG. 8 is a sectional view taken along a line X-X in A of FIG. 7.

To explain the cuff bladder 22 with reference to FIG. 8 which represents the cuff bladder, the first support member 13 shown by A of FIG. 6 is used to make the cuff bladder 22 airtight. Further, the cuff bladder 22 is integrally molded into a hat-like shaped member having a cylindrical portion 22b that elastically deforms between a pressurized state and a depressurized state, and a lid portion 22a that extends from the cylindrical portion 22b and has a flat contact surface 25 that comes into contact with the tragus. The edge of an opening 28 is integrally molded as a flange portion 26. Also, the contact surface 25 can always come into contact with the tragus in a flat state because a first dimension t1 or the thickness of the lid portion 22a is set to be larger than a second dimension t2 or the thickness of the cylindrical portion 22b.

The lid portion 22a is formed into a circular shape, elliptic shape or oval shape, the cylindrically portion 22b is similarly formed into a circular cylindrical shape, elliptic cylindrical shape or oval cylindrical shape, and the cuff members are formed into shapes matching the cylindrical portion.

The cylindrical portion 22b is formed as a bellows member 27 having one or more steps, preferably two steps. When the lid portion is circular, the diameter is set at 15 to 5 mm, preferably about 8 mm. The first dimension t1 is set at 0.4 to 1 mm, preferably about 0.6 mm, and the second dimension t2 is set at 0.1 to 0.8 mm, preferably about 0.3 mm.

Next, A of FIG. 9 is a plan view of the cuff bladders 22, 23, B of FIG. 9 is a front view of the cuff bladders, C of FIG. 9 is a right side view of the cuff bladder, and D of FIG. 9 is a bottom view of the cuff bladder. A of FIG. 10 is a sectional view taken along a line X-X in A of FIG. 9 and B of FIG. 10 is a sectional view taken along a line Y-Y in A of FIG. 9.

Referring to FIGS. 13 and 14, when the lid portions of the cuff bladders 22 and 23 are elliptic or oval, the major axis dimension is 15 to 5 mm, preferably about 10 mm, and the minor axis dimension is 10 to 4 mm, preferably about 8 mm.

Also, in A of FIG. 10, the first dimension t1 is set at 0.4 to 1 mm, preferably about 0.6 mm, and the second dimension t2 is set at 0.1 to 0.8 mm, preferably about 0.3 mm.

Each of the cuff bladders 22 and 23 is integrally molded from an elastic material containing silicone rubber, natural rubber, or a predetermined synthetic resin and having a Shore hardness of 30 to 60, preferably about 50.

As described above, in the hat-like cuff bladders 22 and 23 having the lid portion as the flat contact surface that comes into contact with the tragus 221, the first dimension t1 or the thickness of the lid portion is made to be larger than the second dimension t2 or the thickness of the cylindrical portion. At the time of pressurization, therefore, the contact surface 25 can move to the pressurization position while maintaining the flat state. Also, the contact surface 25 can move to the depressurization position while maintaining the flat state at the time of depressurization as well. Furthermore, the contact surface 25 can move almost parallelly because the cylindrical portion of the cuff bladder has the bellows member (bellows structure) 27.

As explained above, various problems arise when periodically measuring the blood pressure for each predetermined time interval by using the brachium or finger, so stable, highly accurate blood pressure measurement can be performed by using the tragus of the ear as a blood pressure measurement portion.

To continuously measure the blood pressure with high accuracy by a blood pressure measuring apparatus that uses the tragus as a blood pressure measurement portion as described above, pressurized air is supplied to each cuff by a battery-driven pressurizing pump. When the battery-driven pressurizing pump is used, however, long-term measurement is impossible because the battery is rapidly exhausted, so a manual pressurizing pump may also be used. Various fluids can be used as a fluid medium to be pressurized. An example of a gas is air, and examples of a liquid are water, fats and oils including silicone oil, and alcohol. Any of these fluids can be appropriately selected.

Other Embodiments

In the above embodiment, as shown in FIG. 3, only one (the interior of the inner cuff assembly 6) of the pair of cuffs having the arrangement that clamps the tragus 221 has the irradiating portion (LED 20) that irradiates the blood flow in the blood vessel with light, and the light-receiving portion (phototransistor 21) that detects the reflected light from the blood flow.

FIG. 11 is a block diagram showing an example of the arrangement of a blood pressure measuring apparatus according to another embodiment as a photoelectric volume pulse wave blood pressure measuring apparatus, an ear type blood pressure measuring apparatus. In FIG. 24, the same reference numerals as above denote the already explained arrangements or parts, and a repetitive explanation will be omitted. An inner cuff assembly 6 and outer assembly 7 for clamping a tragus 221 respectively incorporate LEDs 20a and 20b as light-emitting portions and phototransistors 21a and 21b as light-receiving portions that detect reflected light.

As described above, it is also possible to arrange sensors in both the inner and outer cuffs, and simultaneously measure the blood pressures on the back side and front side of the tragus. In this arrangement, one cuff can press the blood vessel (arteriole) on the back side of the external ear and its periphery, and the other cuff can press the superficial temporal artery or its branched blood vessel on the front side of the external ear and its periphery.

FIG. 12 is a graph showing the results of blood pressure measurements performed by simultaneous measurements using the inner and outer cuffs. As shown in FIG. 12, as a pressurization curve W1 decreases, a pulse wave signal K1 of the inner cuff 6 changes, and a pulse wave signal K2 of the outer cuff 7 changes. As shown in FIG. 12, the amplitude of the pulse wave signal K1 starts changing largely earlier than the waveform of the pulse wave signal K2. The maximum blood pressure and minimum blood pressure can be measured more accurately by using both of the thus changing pulse wave signals.

Note that the blood pressure in the external ear and its periphery (more specifically, the tragus and its periphery) is measured for the following reason as well.

That is, the blood vessel (arteriole) in the tragus and its periphery is close to the blood vessels in the brain, so it is presumably possible to measure the change in blood pressure resulting from the brain. On the other hand, in the tragus and its periphery, the artery (superficial temporal artery) that directly connects to the heart exists in addition to the blood vessel (arteriole) existing in the cartilage (primarily the tragus) of the ear. In the tragus and its periphery, therefore, a small apparatus can simultaneously measure the blood pressures having different kinds of information (i.e., the blood pressure resulting from the brain and the blood pressure resulting from the heart). The photoelectric volume pulse wave blood pressure measuring apparatus of this embodiment can set the signal level of the pulse wave signal within the predetermined standard range, and can accurately measure the blood pressure in the external ear and its periphery. At the same time, it is possible to shorten the blood pressure measurement time, thereby reducing the physical burden on the user caused by the cuff pressure.

<Arrangement and Assembly Method of Engagement Member>

As shown in A of FIG. 6, both cuff bladder body 22, 23 can be arranged to withstand pressurizing and decompression after being fixed to the cuff member using an O ring. However, it is difficult to ensure air tightness because both cuff bladder bodies 22, 23 and O ring are made of elastic material. Therefore, it is recommended to use a solid engagement member to snap fit the cuff bladders against the cuff member so that air tightness is maintained and also the assembly work is improved.

A of FIG. 13 is an exploded view showing the appearance by which cuff bladders 22 and 23 were installed in cuff material 30, B of FIG. 13 is a sectional view of the cuff assembly body after assembly work is complete.

In these figures, a similar numeral shows the same part or arrangement already explained and the explanation thereof is omitted. First, the LED 20 and the photo transistor 21, shown in a dotted line, is fixed accurately to a predetermined position in the sensor assembly body 31, and a leading wire is extended downwardly as shown and the lead wire is connected with wiring 5. The cuff member 30 is made of injection molded resin material, and has a mounting base 30d for the sensor assembly body 31, and the surrounding portion of the mounting base is connected to a channel 30a. This channel is made as a hollow portion of the pipe 30b on which piping 4 is connected as shown in the Figure.

An outer side 35 having the same or a larger size than the size of first diameter part 44a on the inner surface 44 of the cuff bladders 22 and 23 are formed in the cuff member 30. A jaw part 33 is also formed on the lower portion of the cuff member as shown, and a groove part 34 which becomes one of the engagement parts is formed on the lower portion of the jaw part 33.

Moreover, a flange portion 26 is integrally formed on the edge part of the opening 28 of cuff bladders 22 and 23 outwardly.

On the other hand, another engagement part 38d formed at the end portion of the slope surface 38c is formed on the engagement material 38. This engagement part 38d engages the engagement part formed on the cuff material 30. A pressing surface 38a which suppresses the flange portion 26 is integrally formed.

According to the above-mentioned arrangement, the cuff bladder 22 and 23 are first moved in the direction of the arrow shown in A of FIG. 13 against the cuff material 30 such that the inner surface 44a press-fits to the outer surface 35 or keeping the state in which both engage lightly. Then the engagement material 38 is press-fit as shown in B of FIG. 13, and after this work the flange portion 26 is made to be in its compressed state and surely fixed by the engagement material 38.

After the assembling work is completed, it becomes possible to pressurize and decompress the cuff bladders through the channel 30a. Moreover, because the inner surface 30c of the cuff material 30 has a larger size than the outer surface of sensor assembly body 31, pressurizing and decompression can be done through these gaps. In addition, because a small board 41 connected to leads of each element is already installed as shown in B of FIG. 13, the wiring work can be simplified.

FIG. 14 is a sectional view of the cuff assembly body in accordance with another embodiment wherein same numerals show already referred and explained parts or arrangements, the edge part of small substrate 41 engages with a fingernail part 30k of the cuff material 30 and is fixed to be immovable after the sensor assembly body 31 is inserted from the lower side of the tube part 30f of the cuff material 30. Moreover, the engagement material 38 has a mountain part partially formed on the inner surface and engages with the valley part formed on the outer surface of the cuff member.

In addition, a seal agent 42 is applied on the joint sides between the flange portion and cuff member 30, thus further ensuring air tightness.

According to the arrangement as shown in FIG. 14, by pressurizing the inner potion of the cuff bladder 22, the bellows part 27 can expand such that its contact surface 25 can move from the position shown by the solid line to the dotted line as shown in the Figure and by depressurizing the inner potion of the cuff bladder 22, the contact surface returns to the position shown by the solid line.

<Integrated Arrangement of Tube 4 and Cables 5>

Although the tube 4 and cables 5 are individually installed in FIG. 1, they may become entangled with each other when in use. Since a hollow portion serving as a channel for a fluid including air is formed along the longitudinal direction in the tube 4, it is possible to prevent the cables 5 from being exposed to the outside by passing them through this hollow portion. However, this arrangement requires a sealing portion for ensuring air tightness in a portion where the cables 5 are pulled outside the tube 4, and makes it difficult to secure sealing properties because the tube 4 is freely bendable. This poses the problem of long-term durability, and also interferes with the assembling work.

Accordingly, various arrangements capable of improving the sealing properties and increasing the work efficiency at the same time when integrating the tube 4 and cables 5 were examined.

As a result of this examination, it was concluded that, as in a perspective view of the outer appearance shown in FIG. 15, the best arrangement is to lay the cables 5 along the longitudinal direction on the outer circumferential surface of the tube 4, and cover the cables 5 and tube 4 with the covering member 9 having contraction and expansion properties, thereby integrating the cables 5 and tube 4.

More specifically, the cables 5 connected to the light-emitting element and light-receiving element described earlier are stranded conductors 5a and 5b connected from the light-emitting element and light-receiving element, the tube 4 is molded into a hollow shape as shown in FIG. 17 by using an elastic material containing silicone rubber, natural rubber, or a predetermined synthetic resin, and the covering member 9 is formed into a mesh from a fiber material having a predetermined yarn count. The covering member 9 undergoes a metal coating process for increasing the noise resistance, and is covered with a cover (not shown).

When the tube 4 and cables 5 are thus integrated, they can be freely bent within the circle indicated by the alternate long and short dashed line in FIG. 15 when the user holds one end. In addition, no sealing member is necessary because the cables 5 can be directly extracted from the outer circumferential surface of the tube 4 as shown in FIGS. 13A, 13B. Also, when metal processing is performed on the covering member 9, the noise resistance can be further increased. Even when simply made of cloth, the covering member 9 has the function of protecting the tube 4 and cables 5 from the external environment, thereby making them difficult to damage.

As explained above, when periodically measuring the blood pressure by the conventional blood pressure measuring apparatus using the brachium or finger, various problems occur, however by using the tragus as a blood pressure measuring point, accurate blood pressure measurement becomes possible.

<Cuff Bladder in which Light-Shielding Layer is Formed>

When the LED element 20 and phototransistor 21 for optically detecting a pulse wave are incorporated into the cuff as described above, a portion of the cuff is exposed to the outside when the inner and outer cuffs are attached to the tragus. Under the influence of disturbance light, therefore, accurate blood pressure measurement becomes difficult to perform, particularly when the user goes out and exposes himself or herself to direct sunlight, although there is no serious problem indoors.

A of FIG. 16 shows printing steps of forming a light-shielding layer in the interior of the cuff bladder 22, together with a central sectional view of the cuff bladder 22.

Each of the cuff bladders 22 and 23 is integrally molded from a transparent or light-transmitting elastic material containing silicone rubber, natural rubber, or a predetermined synthetic resin and having a Shore hardness of 30 to 60, preferably about 50. The cuff bladders 22 and 23 are each formed to be airtight with respect to the cuff members, and the contact surface 25 elastically deforms between the position of the pressurized state and the position of the depressurized state as shown in A of FIG. 16 by solid line and dotted line.

When constructed as described above, disturbance light L enters the cuff bladders 22 and 23 because they are transparent, semitransparent, or light-transmitting. Therefore, when a high-sensitivity sensor is used under the sunlight, no accurate blood pressure measurement is possible due to the influence of the sunlight.

Accordingly, as shown in B of FIG. 16, in the cuff bladder 22 used in the inner cuff assembly 6, a light-shielding layer 45 for optically shielding portions except for an opening 46 is continuously formed to an inner wall surface 44 of the cylindrical portion. This makes it possible to irradiate only a blood pressure measurement portion with light by preventing the disturbance light L from entering the interior as shown in FIG. 15, and always detect an accurate pulse wave signal regardless of the location by receiving the reflected light, thereby measuring the blood pressure. Wear of the light-shielding layer 45 in use can be prevented by forming it in the interior as shown in FIG. 15, but it may also be formed outside if a wear resistance can be assured.

When the lid portion 22 of the cuff bladder is formed into a circular shape as described above with reference to FIG. 7, the shape of the opening 46 of the light-shielding layer 45 is formed into a similar small circle. On the other hand, when the contact surface 25 is formed into an elliptic shape or oval shape as described above with reference to FIG. 9, the opening 46 of the light-shielding layer 45 is preferably formed into a circular shape or a similar small elliptic shape or oval shape.

When the contact surface 25 is a circle having a diameter (D1) of 15 to 5 mm, preferably about 8 mm, the diameter of the opening 46 is set at 2 to 8 mm, preferably about 5 mm. When the contact surface 25 is an ellipse or oval having a major axis dimension (D2) of 15 to 5 mm, preferably about 10 mm and a minor axis dimension (D3) of 10 to 4 mm, preferably about 8 mm, the opening 46 is formed into a circle having a diameter of 2 to 8 mm, preferably about 5 mm, or into a circle, ellipse, or oval having an opening area equal to that of the circle. The light-shielding layer 45 having the opening 46 described above can be formed by, for example, two-color injection molding.

FIG. 17 shows printing steps of forming a light-shielding layer in the interior of the cuff bladder 22, together with a central sectional view of the cuff bladder 22. There is a silk screen printing method for printing the light-shielding layer 45 having the opening 46, which is recommended as an inexpensive method.

In step S1 of FIG. 17, the outer appearances of the cuff bladders 22 molded by a rubber molding apparatus and de-flashed are inspected to exclude defective products and select only good products, and the good products are set on a coating tray (not shown). In step S2, degreasing is performed, it is confirmed that there has been no mixing of foreign matter, and a masking sheet 70 having a shape and area corresponding to the opening 46 and including an adhesive surface having slight adhesion is adhered to the center of the back surface of the lid portion of the cuff bladder 22. In this step, a positioning jig is preferably used.

The foregoing is the preparation for coating of a silicone-based binder paint in which a pigment containing carbon black is mixed. Then, the process advances to step S3 to perform an ink coating step.

In this step, the light-shielding layer 45 indicated by the broken lines in FIG. 15 is formed by coating the binder paint by brushing or by using a spray gun. In this stage, the light-shielding layer is not well dried. In a room-temperature drying step in step S4, therefore, the cuff bladder is left to stand for about 1 hr to promote drying, and the masking 70 is removed by using a tool such as a forceps.

After that, the process advances to step S5, the dried cuff bladders are placed in an oven, and oven processing for baking coating is performed at about 200° C. for about 10 to 15 min. Then, the coating tray is removed from the oven. In a finish inspection step in step S6, outer appearance inspection is performed to inspect foreign matter, overflow of the paint to the opening 46, uneven coating, and the like, thereby selecting good products and terminating the process.

The cuff bladder 22 completed through the above steps is used as it is attached as shown in FIG. 7.

Note that although the foregoing are examples of the steps of forming the light-shielding layer inside the cuff bladder, almost similar steps can be used to form the light-shielding layer outside the cuff bladder. In addition, the two-color injection molding method described previously makes the coating step unnecessary, but a metal mold is complicated and expensive. Therefore, a method to be used will be determined in accordance with the number of cuffs to be manufactured.

<Arrangement of One-Way Moving Member>

A of FIG. 18 is a sectional view showing that the cuff assembly is provided at the distal end of the adjustment screw mounted on the third support member 15 with some degree of freedom, B of FIG. 18 is a sectional view showing that the cuff assembly is provided at the distal end of the one-way moving member or brushing member.

As described above, the clamping width adjusting screw 11 pivots forward and backward by threadably engaging the male screw portion formed on the outer circumferential surface of the main body of the adjusting screw 11 with the female screw hole formed in the second holding member 14. This allows the outer cuff assembly having the cuff bladder 23 to freely move and turn its head. If the movement stroke of the outer cuff assembly is large, however, a short-tempered person or a person having trouble in fingers may think it troublesome to rotate the adjusting screw 11. Instead of the adjusting screw 11, therefore, it is also possible to use a brushing bush 49 that is a unidirectional moving member capable of moving to a desired position at once regardless of the length of the movement stroke of the outer cuff assembly.

That is, as shown in B of FIG. 18, the brushing bush 49 as a unidirectional moving member is obtained by integrally molding a plurality of elastically deformable flanges 49b on the outer circumferential surface and a ball bearing 49a at the end portion by using a predetermined nylon-based resin material. The diameter of the flange 49b is set larger than the inner diameter of a hole 15a formed in the other end of a third holding member 15. Accordingly, when the brushing bush 49 is inserted into the hole 15a in one direction indicated by the arrow, the three flanges 49b obliquely deform in the direction opposite to the insertion direction as shown in Fig., and abut against the inner circumferential surface of the hole 15a by the elastic deformation force. The outer cuff assembly can be held in this state. Also, when the brushing bush 49 is pulled with a force larger than that for insertion, a stopper (not shown) abuts against the edge of the hole 15a to allow the brushing bush 49 to be pulled out to the original position. Note that the brushing bush 49 has an arrangement close to that of a product also called a one-touch fastener.

<Arrangement of the Support Member>

The tragus has great individual differences in relative position with respect to the external ear hole, shape, size, sex, etc. The tragus also has great individual differences based on race and age, and therefore it becomes difficult to maintain the inner and outer cuffs to surely keep in contact with the tragus.

Therefore, in addition to the portion for clamping the tragus and the portion for filling the space between the antihelix and the auricular, if the installation part 3 has a ear hook 51 to be mounted on the ear extended portion having the cartilage, it becomes possible to cope with the individual differences.

FIG. 19 is an exploded view of installation part 3, where same numeral shows already referred and explained parts and explanation thereof is omitted. Referring the FIG. 19, the outer cuff comprises the first outer cuff 7 and the second outer cuff 8 to be located vertically with respect to the tragus, where the cuff 7 and 8 are fixed to the cuff material 30 having the channel which leads to piping 4. Engagement hole 47 is formed on the center portion of the cuff material 30. Moreover, a female screw hole 15a is formed on the end portion of the support member 15, and a width adjustment screw 11 as a means for clamping width adjustment part is screwed into the female screw hole 15a as shown. On the distal end of the width adjustment screw 11, a ball bearing 11a to be snap-fitted into the engagement hole 47 is integrally formed so that the cuff material 30 can move freely after the engagement to do the neck movement.

On the other hand, a first protruding portion 54 is extended towards the ear hole from the shape part 52 having a strawberry configuration to be filled in the space between the auricular concha to the antihelix. A second protruding portion 55 is extended vertically with respect to the first protruding portion from this shape part so that second protruding portion can be located above the tragus. The first and the second protruding portions are integrally molded with the shape part or each is prepared as individual parts and is fixed to the shape part as shown in the Figure.

In addition, an ear hook part 51 having the same shape as the extended portion of the helix is integrally formed upwardly from this shape part 52, thus forming the whole integral member 50 as shown.

The above-mentioned inner cuff 6 is supported at the end portion of the first protruding portion 54 as shown in the FIG. 19. Natural inserting operation into the external ear becomes possible if this inner cuff has an oval shape and is inserted along the longitudinal direction of the oval shape. Therefore, the inner cuff is fixed to the first protruding portion 54 so that natural insertion into the ear hole can be realized.

This inner cuff 6 can be made to adjust the degree of invasion to the ear hole or can be made to realize a free rotation with respect to the first protruding portion 54 as shown in Figure. This inner cuff is connected with tube 4 through internal tube 53 (shown by the dotted line) of the first protruding portion 54, so that the pressurization and the decompression are possible.

On the end surface of the second protruding portion 55 of shape part 52, several groove parts 55b are radially formed from the screw hole 55a as a center as shown in the Figure. Installation part 3 is completed by inserting the first adjustment screw 18 into the screw hole 55a formed in the above-mentioned support member 15 and screwing tightly. Moreover, the end portion 52a of the shape part 52 having the strawberry configuration constitutes the antihelix. The shape part having various sizes may be prepared because individual differences between the auricular concha and the antihelix is great as has already been discussed.

Next, FIG. 20 is a perspective view of the installation portion 3 after assembly thereof is completed. FIG. 21 is a perspective view showing the state how the installation portion 3 is used. In FIGS. 20 and 21, same numerals referred show the same arrangement or part already explained and the explanation thereof is omitted. As shown in FIGS. 20 and 21, one inner cuff 7 is attached to the support member 15 using the width adjustment screw 11.

According to this arrangement, if the first adjustment screw 18 is loosened by using a tool, the outer cuff 7 can be rotated and moved in the up and down direction as shown by arrow D3 so that the outer cuff corresponds to the position of the tragus. Then, by tightening the screw 18 at the fixed position, the outer cuff can be locked at a position which opposes the inner cuff. At the same time, by adjusting the width adjustment screw 11, the outer cuff 7 can be moved in the back and forth directions as shown by an arrow D1, and finally the outer cuff 7 is fixed at a position where the user does not feel the pain.

As has been mentioned above, because the inner and outer cuff 6 and 7 can be adjusted to correctly come into contact with the tragus, it becomes possible to maintain the state such that both inner and outer cuffs are installed properly in a stabilizing state at the tragus which changes greatly between individuals.

On the other hand, in order to mold the shape part 52 and the ear hook part 51 having a shape as shown in Figure, resin materials such as polycarbonate, ABS resin, POM (poly acetal), and PPS, etc., can be used. Moreover, these materials are not limited, and other resin materials suitable for mass production, dimensional stability, and cost, etc., can be used as a material. So-called high breed compositions using light metals, tree, paper, and various materials combined also can be used.

Moreover, the color of the shape part may be made to correspond to various sizes, for example, orange color for the hospital use, blue color for general use and white color for children.

<External View of Cuff Installation>

FIG. 22 shows the appearance when installation part 3 of blood pressure measurement apparatus 1 is installed into the tragus 221. And FIG. 23 is the outer appearance of the installation part 3.

In the FIGS. 22 and 23, one outer cuff 7 is installed into the support member 15 by using the width adjustment screw 11.

Here, the support means comprising the support member 15, the first protrusion part 54, and the second protrusion part 55 formed from the shape part 52 of the integral member 50 has a letter "U" shape as shown in the figures. The shape of the letter "U" means that only a portion of the support member is open ended and portions (or support member 15 and the first protrusion part 54) where the inner cuff assembly body 6 and the outer cuff assembly body 7 are mounted are parallel. The inner cuff assembly body 6 is mounted on the first protrusion part 54, and a screw hole 15a for clamping width adjustment screw 11 as the clamping width adjustment mechanism is provided in the support member 15. Moreover, the outer cuff assembly body 7 is attached at the end point of the clamping width adjustment screw 11. As a result, the inner cuff assembly body 6 and outer cuff assembly body 7 can be made to oppose each other (when the outer cuff assembly body 7 does not do the neck moving motion and stays at a basic position). Also, if the clamping width adjustment screw 11 is rotated clockwise the clamping width narrows, and if rotated counter clockwise the clamping width widens.

According to this arrangement, if the first adjustment screw 18 is loosened by using a tool, the outer cuff 7 can be rotated and moved in the up and down direction as shown by arrow D3 so that the outer cuff corresponds to the position of the tragus. Then by tightening the screw 18 at the fixed position the outer cuff can be locked at a position which opposes the inner cuff. At the same time, by adjusting the width adjustment screw 11, the outer cuff 7 can be moved in the back and forth directions as shown by an arrow D1, and finally the outer cuff 7 is fixed at a position where the user does not feel the pain.

As has been mentioned above, because the inner and outer cuff 6 and 7 can be adjusted to correctly come into contact with the tragus, it becomes possible to maintain a state such that both inner and outer cuffs are installed properly in a stabilizing state at the tragus which changes greatly between individuals.

On the other hand, in order to mold the shape part 52 and the ear hook part 51 having a shape as shown in Figure, resin materials such as polycarbonate, ABS resin, POM (poly acetal), and PPS, etc., can be used. Moreover, these materials are not limited, and other resin materials suitable for mass production, dimensional stability, and cost, etc., can be used as a material. So-called hybrid compositions using light metals, tree, paper, and various materials combined also can be used.

Moreover, color of the shape part may be made to correspond to various sizes, for example orange color for the hospital use, blue color for general use and white color for children.

In addition, according to this embodiment, the main body 2 of the blood pressure measuring apparatus is installed onto the ear hook part 51. In this main body, a circuit necessary for measuring the blood pressure, an air exhaust valve, and a pressure pump, etc., are incorporated. Moreover, on the exterior side of the main body 2, display part (LCD) 114 for the display of information on the blood pressure, etc., a buzzer (speaker) 115 to output the warning sound and the operation sound, etc., and bottoms as a controlling element 116 are provided. This main body 2 of the blood pressure measuring apparatus is made to match the shape of the user's ear, and has a shape just like a small hearing aid.

For instance, one side surface 2a of the main body 2 of the blood pressure measuring apparatus has a flat or a smooth curved surface such that it corresponds to the shape of the side of the head at the back of the ear. On the other hand, the other side surface 2b of the blood pressure measuring apparatus may have a swelling shape to some degree in order to accommodate parts for the blood pressure measurement. In other words, the radius of curvature on the side surface 2a is larger than that of the side surface 2b. Also, the shape of the side surface 2b is decided based on the number and sizes of the accommodated parts, therefore, if the number of the parts is small, the side surface 2b becomes more flat. In addition, it is needless to say that main body 2 can be miniaturized.

The tube 4 and wiring 5 are extended from the circuit board and the portion incorporated in the main body 2 and they are connected with the inner cuff assembly body 6 and the outer cuff assembly body 7 via an ear hook part 50 and shape part 52. The tube 4 is shown by a chain line in FIG. 24, and wiring 5 is shown by a one point dotted chain line.

Moreover, the tube 4 diverges at a mid point of the ear hook part 51, and one tube projects outside the ear hook part 51. Also, the thus projected tube 4 is connected to the outer cuff assembly body 7, for example.

<Arrangement of Holding Member 3>

The tragus has great individual differences in relative position with respect to the external ear hole, shape, size, and sex, etc. The tragus also has great individual differences based on race and age, and therefore it becomes difficult to maintain the inner and outer cuffs to surely keep in contact with the tragus.

Accordingly, in addition to the portions of the holding member 3 for clamping the tragus, and the shape part to be inserted into a space between the auricular concha and the antihelix, if the ear hook to be mounted on the extended portion having the cartilage located between the head side and the ear is provided to the apparatus, the apparatus can cope with the individual differences.

FIG. 24 is an exploded view of the holding member 3. Referring this figure, the outer cuff 7 is attached to the clamping width adjustment screw 11. An engagement hole 47 is formed on the center portion of the side surface of the outer cuff 7.

Moreover, a female screw hole 15a is formed on the end portion of the support member 15, and the width adjustment screw 11 which functions as a clamping width controlling means is screwed into the female screw hole as shown in FIG. 24. Moreover, a ball bearing 11a with which the engagement hole 47 is snap fitted is formed on the end point of the adjustment screw 11 such that the outer cuff 7 can move freely with the neck moving motion.

On the other hand, a first protruding portion 54 is extended towards the ear hole from the shape part 52 having a strawberry configuration to be filled in the space between the auricular concha to the antihelix. A second protruding portion 55 is extended vertically with respect to the first protruding portion from this shape part so that second protruding portion can be located above the tragus. The first and the second protruding portions are integrally molded with the shape part or each is prepared as an individual part and is fixed to the shape part as shown in the Figure.

In addition, an ear hook part 51 having the same shape as the extended portion of the helix is integrally formed upwardly from this shape part 52, thus forming the whole integral member 50 as shown.

The above-mentioned inner cuff 6 is supported at the end portion of the first protruding portion 54 as shown in the FIG. 24. Natural inserting operation into the external ear becomes possible if this inner cuff has an oval shape and is inserted along the longitudinal direction of the oval shape. Therefore, the inner cuff is fixed to the first protruding portion 54 so that natural insertion into the ear hole can be realized.

This inner cuff 6 can be made to adjust the degree of invasion to the ear hole or can be made to realize free rotation with respect to the first protruding portion 54 as shown in Figure. This inner cuff is connected with tube 4 through an internal tube 53 (shown by dotted line) of the first protruding portion 54, so that the pressurization and the decompression are possible.

On the end surface of the second protruding portion 55 of shape part 52, several groove parts 55b are radially formed from the screw hole 55a as a center as shown in the Figure. Holding member 3 is completed by inserting the first adjustment screw 18 into the screw hole 55a formed in the above-mentioned support member 15 and screwing tightly. Moreover, the end portion 52a of the shape part 52 having the strawberry configuration constitutes the antihelix. The shape part having various sizes may be prepared because individual differences between the auricular concha and the anti-helix is great as has already been discussed.

<Whole Arrangement of Integral Member 50>

As mentioned above, the integral member 50 comprises the ear hook part 51, the shape part 52 having the first protruding portion 54 and the second protruding portion 55.

The contact portion of the ear hook 51 that contacts the helix 225 (helix contact portion) and/or the contact portion (the end portion 52a) of the shape part 52 that at least contacts the antihelix 224 are made of softer materials than other parts of the integral member 50. The core of the shape part 52 may be made of a hard material and the surface layer may be made of a soft material.

For example, materials such as a silicone rubber, a styrene, a urethane system, an olefinic elastomeric material, PE (polyethylene), PP (polypropylene), POM (polyacetal resin), and various rubbers may be used for the ear contact part 51a and the end portion 52a. For the other portion, a harder material such as PC (polycarbonate), ABS (acrylic nitrile styrene-butadiene rubber), POM (polyacetal) system and PPS (poly phenylene sulfide) resin, etc., may be used. In other words, a hard material is used to obtain a constant rigidity throughout the entire area of the integral member 50, and a soft material is used for the area that corresponds to the user's ear. The first protruding portion 54 and the second protruding portion 55 and the core of the integral member 50 may be made of a hard material to obtain a constant rigidity, and a soft material may be used to cover the whole surface area.

In order to manufacture the integral member 50, two color injection molding technique may be used. This method uses two resin materials with different melting points (above-mentioned hard material and software material) that are injected into a mold through a mold shutter. The resin materials having a high melting point are injected into the mold through the mold shutter first, and after the injected material is hardened, the mold shutter is removed and resin material having a low melting point is injected into the mold. Thus the integral member 50 is integrally molded.

As mentioned above, the stability of the installation is improved because the part which comes in contact with the ear is made of a soft material without depending on an individual ear configuration, and it reduces a psychological burden of the user thus enabling installation for a long period of time.

The blood pressure measuring apparatus 1 is thus constituted by attaching the main body 2 to the end portion of the ear hook portion 51 of the integral member 50.

<Internal Arrangement of the Main Body 2 for the Blood Pressure Measuring Apparatus>

FIG. 25 is an actual plan view of the main body 2 of the blood pressure measuring apparatus, in which the lid is removed from the apparatus main body 2.

Electronic parts for measuring the blood pressure are mounted on a substrate board 140 having a mounting area that occupies an internal space. On the other hand, a pressure pump 108, a condenser tank 117, a slow exhaust valve 105, a quick exhaust valve 104 are connected to tube 4 that is integrally formed. Each part is arranged as shown in the figure, and a power supply part 121 which consists of a mercury button battery can be installed in parallel. The power supply unit 121 containing a chargeable secondary battery that can be repetitively used or commercially available AAA cells that are readily obtainable can be simply exchanged by opening and closing a lid (not shown).

The tube 4 is connected with a pressure sensor 106 installed on the substrate board 140, the rapid release valve 104, and the minute release valve 105 of and the pressure pump 108. Moreover, wiring 5 is connected with the light energy control part 118, filter amplifier 109, LCD 114, buzzer 115, and final controlling element 116 on the board 140.

The present invention is not limited to the above embodiments, and various changes and modifications can be made without departing from the spirit and scope of the invention. Therefore, to apprise the public of the scope of the present invention, the following claims are made.

The invention claimed is:

1. A blood pressure measuring apparatus comprising:
   an inner cuff to be inserted into an ear hole, and an outer cuff to be positioned outside a tragus;
   holding means for holding said inner cuff and said outer cuff;
   pulse wave detecting means incorporated into at least one of said inner cuff and said outer cuff to detect a pulse wave signal from blood flowing through a blood vessel;
   pressurizing/depressurizing means for pressurizing and depressurizing said inner cuff and said outer cuff by using a fluid, after said inner cuff and said outer cuff clamp the tragus;
   a tube connected from said inner cuff and said outer cuff to said pressurizing/depressurizing means to supply the fluid;
   pressure detecting means connected to said tube to detect pressures of said inner cuff and said outer cuff; and
   blood pressure measurement control means for measuring a blood pressure value from the pulse wave signal,
   wherein said holding means comprises;
   a shape part to be installed in a space between an auricular concha and an antihelix,
   a first protrusion extended from said shape part such that said first protrusion is directed towards the ear hole,
   a second protrusion extended from said shape part such that said second protrusion is nearly right-angled with respect to said first protrusion and said second protrusion steps over the tragus,
   an integral member having an ear hook that is extended from said shape part, said ear hook being integrally made with said integral member or made as an independent member,
   wherein said integral member supports said inner cuff at an end portion of said first protrusion,
   said integral member fixes a support member at an end portion of said second protrusion, said outer cuff is attached to said support member through a clamping width adjustment part that makes a clamping width adjustment against the tragus possible, and said outer cuff is made of a first outer cuff and a second outer cuff, said first outer cuff and said second outer cuff are fixed to a cuff member having a channel communicating said tube, such that said first outer cuff and said second outer cuff are located in the up and down directions with respect to the tragus, said cuff member is attached at an end portion of said support member through said clamping width adjustment part.

2. A blood pressure measuring apparatus according to claim 1, wherein said support member is attached to said second protrusion such that said support member is adjustable in the up and down directions with respect to the tragus.

3. A blood pressure measuring apparatus according to claim 1, wherein said inner cuff is fixed to said first protrusion such that said inner cuff can rotate and the degree of invasion into the ear hole is adjustable, and said inner cuff can be pressurized and depressurized through an inner tube provided in said first protrusion.

4. A blood pressure measuring apparatus according to claim 1, wherein said clamping width adjustment part comprises a ball bearing part provided on the end portion, wherein said ball bearing part supports said outer cuff such that said outer cuff can move with neck movement.

5. A blood pressure measuring apparatus according to claim 1, wherein a first adjustment screw for adjusting said support member in the up and down directions with respect to said second protrusion is provided, wherein said first adjustment screw maintains a state after the adjustment.

6. A blood pressure measuring apparatus according to claim 1, wherein said clamping width adjustment part is a one direction movement member comprising a male screw screwed into a female hole formed at the other end of said support member, or a one direction movement member comprising a plurality of flexible jaws on the outer surface which keeps the inserted state after being inserted into a hole.

7. A blood pressure measuring apparatus according to claim 1, wherein said pulse wave detecting means, said pressurizing/depressurizing means and said blood pressure measurement control means are incorporated into a main body of the apparatus, wherein main body and said holding means supporting said inner cuff and said outer cuff are connected by said tube and a wire connected between said pulse wave detecting means and said blood pressure measurement control means.

8. A blood pressure measuring apparatus comprising:
an inner cuff to be inserted into an ear hole, and an outer cuff to be positioned outside a tragus;
holding means for holding said inner cuff and said outer cuff;
pulse wave detecting means incorporated into at least one of said inner cuff and said outer cuff to detect a pulse wave signal from blood flowing through a blood vessel;
an ear hook part extended from said holding means;
a blood pressure measurement main body directly attached to said ear hook part, and positioned behind the rear portion of an auricle when installed;
wherein said blood pressure measurement main body comprises;
pressurizing/depressurizing means for pressurizing and depressurizing said inner cuff and said outer cuff by using a fluid;
blood pressure measurement control means for measuring a blood pressure value from the pulse wave signal;
wherein said inner cuff, said outer cuff and said pressurizing/depressurizing are connected by a fluid sending tube for sending said fluid, and
wherein said fluid sending tube is incorporated in said ear hook part.

9. A blood pressure measuring apparatus according to claim 8, wherein said holding means comprises;
a shape part to be installed in a space between an auricular concha and an antihelix,
a first protrusion extended from said shape part such that said first protrusion is directed towards the ear hole,
a second protrusion extended from said shape part such that said second protrusion is nearly right-angled with respect to said first protrusion and said second protrusion steps over the tragus,
a support member formed on an end portion of said second protrusion, and
an integral member having said ear hook that is integrally extended from said shape part.

10. A blood pressure measuring apparatus according to claim 9, wherein said support member has a clamping width adjustment part at an end portion for adjusting the clamping width of said outer cuff and said outer cuff.

11. A blood pressure measuring apparatus according to claim 10, wherein said clamping width adjustment part has a neck movement mechanism at the end potion wherein said outer cuff can move with neck movement.

12. A blood pressure measuring apparatus according to claim 9, wherein said support member is attached to said second protrusion such that said support member is adjustable in the up and down directions with respect to the tragus.

13. A blood pressure measuring apparatus according to claim 8, wherein an ear contact point against the antihelix of said shape part is made of softer materials than other parts.

14. A blood pressure measuring apparatus according to claim 8, wherein an ear contact point of said ear hook is made of softer materials than other parts.

15. A blood pressure measuring apparatus according to claim 8, wherein said main body has a larger curve radius at the user's head contact side than the user's head non-contact side.

* * * * *